(12) United States Patent
Tedesco et al.

(10) Patent No.: US 7,999,081 B2
(45) Date of Patent: Aug. 16, 2011

(54) ANTI-C5 ALPHA ANTIBODIES

(75) Inventors: Francesco Tedesco, Trieste (IT); Roberto Marzari, Trieste (IT)

(73) Assignee: Adienne SRL, Bergamo (IT)

( * ) Notice: Subject to any disclaimer, the term of this patent is extended or adjusted under 35 U.S.C. 154(b) by 1766 days.

(21) Appl. No.: 10/521,109

(22) PCT Filed: Jul. 10, 2003

(86) PCT No.: PCT/EP03/07487
§ 371 (c)(1),
(2), (4) Date: Jan. 11, 2005

(87) PCT Pub. No.: WO2004/007553
PCT Pub. Date: Jan. 22, 2004

(65) Prior Publication Data
US 2006/0115476 A1    Jun. 1, 2006

(30) Foreign Application Priority Data

Jul. 11, 2002   (IT) .............................. MI2002A1527

(51) Int. Cl.
*C07K 16/36* (2006.01)
*C07K 16/00* (2006.01)
*A61K 39/395* (2006.01)

(52) U.S. Cl. ............. 530/388.25; 530/387.1; 530/387.3; 530/387.9; 530/388.2; 424/130.1; 424/133.1; 424/139.1; 424/145.1; 424/158.1

(58) Field of Classification Search .................. None
See application file for complete search history.

(56) References Cited

U.S. PATENT DOCUMENTS

| | | | | |
|---|---|---|---|---|
| 5,770,429 | A | * | 6/1998 | Lonberg et al. ............... 435/328 |
| 6,355,245 | B1 | * | 3/2002 | Evans et al. ................ 424/145.1 |
| 2003/0039649 | A1 | * | 2/2003 | Foote .......................... 424/141.1 |
| 2004/0001822 | A1 | * | 1/2004 | Levanon et al. ........... 424/130.1 |

FOREIGN PATENT DOCUMENTS

WO    WO 02/30985    4/2002

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Lederman et al., Molecular Immunology 28: 1171-1181, 1991.*
Li et al., PNAS 77: 3211-3214, 1980.*
Evans et al., "In Vitro and In Vivo Inhibition of Complement Activity by a Single-Chain Fv Fragment Recognizing Human C5," Mol. Immunol. 32:1183-1195, 1995.
Fitch et al., "Pharmacology and Biological Efficacy of a Recombinant, Humanized, Single-Chain Antibody C5 Complement Inhibitor in Patients Undergoing Coronary Artery Bypass Graft Surgery with Cardiopulmonary Bypass," Circulation 100:2499-2506, 1999.
Thomas et al., "Inhibition of Complement Activity by Humanized Anti-C5 Antibody and Single-Chain Fv," Mol. Immunol. 33:1389-1401, 1996.
Wang et al., "Amelioration of Lupus-like Autoimmune Disease in NZB/W F1 Mice After Treatment with a Blocking Monoclonal Antibody Specific for Complement Component C5," Proc. Natl. Acad. Sci. U.S.A. 93:8563-8568, 1996.
Bui, H.H., et al., "Development of an epitope conservancy analysis tool to facilitate the design of epitope-based diagnostics and vaccines," *BMC Bioinformatics* 8:361, BioMed Central Ltd., England (Sep. 2007).
Collet, X., et al., "Evolution of mammalian apolipoprotein A-I and conservation of antigenicity: correlation with primary and secondary structure," *J. Lipid Res.* 38(4):634-44, American Society for Biochemistry and Molecular Biology, United States (Apr. 1997).
Fredslund, F., et al., "Structure of and influence of a tick complement inhibitor on human complement component 5," *Nat. Immunol.* 9(7):753-60, Nature Publishing Group, United States (Jul. 2008; Epub: Jun. 2008).
Jemmerson, R., et al., "Analysis of an evolutionarily conserved antigenic site on mammalian cytochrome c using synthetic peptides," *Proc. Natl. Acad. Sci. USA* 82(5):1508-12, National Academy of Sciences, United States (Mar. 1985).
Marzari, R., et al., "The cleavage site of C5 from man and animals as a common target for neutralizing human monoclonal antibodies: in vitro and in vivo studies," *Eur. J. Immunol.* 32(10):2773-82, Wiley-VCH Verlag GmbH & Co., Germany (Oct. 2002).
Potter, N. T., et al., "Identification of an antigenic determinant within the phylogenetically conserved triprolyl region of myelin basic protein," *J. Immunol.* 136(2):516-20, The American Association of Immunologists, United States (Jan. 1986).
Sandoval, A., et al., "Distal recognition site for classical pathway convertase located in the C345C/netrin module of complement component C5," *J. Immunol.* 165(2):1066-73, The American Association of Immunologists, United States (Jul. 2000).

* cited by examiner

*Primary Examiner* — Phillip Gambel
(74) *Attorney, Agent, or Firm* — Sterne, Kessler, Goldstein & Fox P.L.L.C.

(57) ABSTRACT

The present invention refers to recombinant antibodies of human origin specific for the C5 component of the activated complement and characterised by the ability to inhibit the conversion of the C5 alpha chain to C5*a* and C5*b*. Moreover the present invention refers to the nucleotide sequences coding for such antibodies and to the therapeutic use of both polypeptide and nucleotide sequences, in particular for the therapy of diseases involving tissue damage deriving from uncontrolled activation of the complement system.

18 Claims, 11 Drawing Sheets

SEQUENCE LISTING

<160> NUMBER OF SEQ ID NOS: 35

<210> SEQ ID NO 1
<211> LENGTH: 342
<212> TYPE: DNA
<213> ORGANISM: Homo sapiens
<220> FEATURE:
<221> NAME/KEY: CDS
<222> LOCATION: (1)..(342)
<223> OTHER INFORMATION: Light chain of the TS-A12/22 antibody

<400> SEQUENCE: 1

```
gac atc cgg atg acc cag tct cca gac tcc ctg gct gtg tct ctg ggc       48
Asp Ile Arg Met Thr Gln Ser Pro Asp Ser Leu Ala Val Ser Leu Gly
1               5                   10                  15 gag agg gcc acc atc aac tgc aag tcc agc cag agt gtt tta tac agc       96
Glu Arg Ala Thr Ile Asn Cys Lys Ser Ser Gln Ser Val Leu Tyr Ser
            20                  25                  30 tcc aac aat aag aac tac tta gct tgg tac cag cag aaa cca gga cag      144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc      192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa      288
Ile Ser Ser Leu Gln Ala Glu Asp Val Ala Val Tyr Tyr Cys Gln Gln
                85                  90                  95 tat tat agt act cct cag ctc act ttc ggc gga agg acc aaa gtg gat      336
Tyr Tyr Ser Thr Pro Gln Leu Thr Phe Gly Gly Arg Thr Lys Val Asp
            100                 105                 110 atc aaa                                                              342
Ile Lys
```

<210> SEQ ID NO 2
<211> LENGTH: 114
<212> TYPE: PRT
<213> ORGANISM: Homo sapiens

<400> SEQUENCE: 2

```
Asp Ile Arg Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

```
Ile Ser Ser Leu Gln Ala Glu Asp Val Ala Val Tyr Tyr Cys Gln Gln
                85                  90                  95

Tyr Tyr Ser Thr Pro Gln Leu Thr Phe Gly Gly Arg Thr Lys Val Asp
            100                 105                 110

Ile Lys

<210> SEQ ID NO 3
<211> LENGTH: 345
<212> TYPE: DNA
<213> ORGANISM: Homo sapiens
<220> FEATURE:
<221> NAME/KEY: CDS
<222> LOCATION: (1)..(345)
<223> OTHER INFORMATION: Heavy chain of the TS-A12/22 antibody

<400> SEQUENCE: 3 cag gta cag ctg cag cag tca gag gga ggc gtg gtc cag cct ggg agg        48
Gln Val Gln Leu Gln Gln Ser Glu Gly Gly Val Val Gln Pro Gly Arg
1               5                   10                  15 tcc ctg aga ctc tcc tgt gca gcg tct gga ttc acc ttc agt agc tat        96
Ser Leu Arg Leu Ser Cys Ala Ala Ser Gly Phe Thr Phe Ser Ser Tyr
            20                  25                  30 ggc atg aac tgg gtc cgc cag gct cca ggg aag ggg ctg gag tgg gtt       144
Gly Met Asn Trp Val Arg Gln Ala Pro Gly Lys Gly Leu Glu Trp Val
        35                  40                  45 tca tac att agt agt agt agt agt acc ata tac tac gca gac tct gtg       192
Ser Tyr Ile Ser Ser Ser Ser Ser Thr Ile Tyr Tyr Ala Asp Ser Val
    50                  55                  60 aag ggc cga ttc acc atc tcc aga gac aat tcc aag aac acg ctg tat       240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt       288
Leu Gln Met Asn Ser Leu Arg Ala Glu Asp Thr Ala Val Tyr Tyr Cys
                85                  90                  95 gcg aga ggg cct ggt atg gac gtc tgg ggc caa ggg acc acg gtc acc       336
Ala Arg Gly Pro Gly Met Asp Val Trp Gly Gln Gly Thr Thr Val Thr
            100                 105                 110 gtc tcc tca                                                           345
Val Ser Ser
        115

<210> SEQ ID NO 4
<211> LENGTH: 115
<212> TYPE: PRT
<213> ORGANISM: Homo sapiens

<400> SEQUENCE: 4

Gln Val Gln Leu Gln Gln Ser Glu Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Pro Gly Met Asp Val Trp Gly Gln Gly Thr Thr Val Thr
```

```
                          100                 105                 110
Val Ser Ser
        115

<210> SEQ ID NO 5
<211> LENGTH: 750
<212> TYPE: DNA
<213> ORGANISM: Homo sapiens
<220> FEATURE:
<221> NAME/KEY: CDS
<222> LOCATION: (1)..(750)
<223> OTHER INFORMATION: scFv

<400> SEQUENCE: 5 gac atc cgg atg acc cag tct cca gac tcc ctg gct gtg tct ctg ggc      48
Asp Ile Arg Met Thr Gln Ser Pro Asp Ser Leu Ala Val Ser Leu Gly
1               5                   10                  15 gag agg gcc acc atc aac tgc aag tcc agc cag agt gtt tta tac agc      96
Glu Arg Ala Thr Ile Asn Cys Lys Ser Ser Gln Ser Val Leu Tyr Ser
            20                  25                  30 tcc aac aat aag aac tac tta gct tgg tac cag cag aaa cca gga cag     144
Ser Asn Asn Lys Asn Tyr Leu Ala Trp Tyr Gln Gln Lys Pro Gly Gln
        35                  40                  45 cct cct aag ctg ctc att tac tgg gca tct acc cgg gaa tcc ggg gtc     192
Pro Pro Lys Leu Leu Ile Tyr Trp Ala Ser Thr Arg Glu Ser Gly Val
    50                  55                  60 cct gac cga ttc agt ggc agc ggg tct ggg aca gat ttc act ctc acc     240
Pro Asp Arg Phe Ser Gly Ser Gly Ser Gly Thr Asp Phe Thr Leu Thr
65                  70                  75                  80 atc agc agc ctg cag gct gaa gat gtg gca gtt tat tac tgt cag caa     288
Ile Ser Ser Leu Gln Ala Glu Asp Val Ala Val Tyr Tyr Cys Gln Gln
                85                  90                  95 tat tat agt act cct cag ctc act ttc ggc gga agg acc aaa gtg gat     336
Tyr Tyr Ser Thr Pro Gln Leu Thr Phe Gly Gly Arg Thr Lys Val Asp
            100                 105                 110 atc aaa tcc gga ggg tcg acc ata act tcg tat aat gta tac tat acg     384
Ile Lys Ser Gly Gly Ser Thr Ile Thr Ser Tyr Asn Val Tyr Tyr Thr
        115                 120                 125 aag tta tcc tcg agc ggt acc cag gta cag ctg cag cag tca gag gga     432
Lys Leu Ser Ser Ser Gly Thr Gln Val Gln Leu Gln Gln Ser Glu Gly
    130                 135                 140 ggc gtg gtc cag cct ggg agg tcc ctg aga ctc tcc tgt gca gcg tct     480
Gly Val Val Gln Pro Gly Arg Ser Leu Arg Leu Ser Cys Ala Ala Ser
145                 150                 155                 160 gga ttc acc ttc agt agc tat ggc atg aac tgg gtc cgc cag gct cca     528
Gly Phe Thr Phe Ser Ser Tyr Gly Met Asn Trp Val Arg Gln Ala Pro
                165                 170                 175 ggg aag ggg ctg gag tgg gtt tca tac att agt agt agt agt acc         576
Gly Lys Gly Leu Glu Trp Val Ser Tyr Ile Ser Ser Ser Ser Thr
            180                 185                 190 ata tac tac gca gac tct gtg aag ggc cga ttc acc atc tcc aga gac     624
Ile Tyr Tyr Ala Asp Ser Val Lys Gly Arg Phe Thr Ile Ser Arg Asp
        195                 200                 205 aat tcc aag aac acg ctg tat ctg caa atg aac agc ctg aga gcc gag     672
Asn Ser Lys Asn Thr Leu Tyr Leu Gln Met Asn Ser Leu Arg Ala Glu
    210                 215                 220 gac acg gct gtg tat tac tgt gcg aga ggg cct ggt atg gac gtc tgg     720
Asp Thr Ala Val Tyr Tyr Cys Ala Arg Gly Pro Gly Met Asp Val Trp
225                 230                 235                 240 ggc caa ggg acc acg gtc acc gtc tcc tca                             750
Gly Gln Gly Thr Thr Val Thr Val Ser Ser
                245                 250
```

<210> SEQ ID NO 6
<211> LENGTH: 250
<212> TYPE: PRT
<213> ORGANISM: Homo sapiens

<400> SEQUENCE: 6

Asp Ile Arg Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Gln Leu Thr Phe Gly Gly Arg Thr Lys Val Asp
            100                 105                 110

Ile Lys Ser Gly Gly Ser Thr Ile Thr Ser Tyr Asn Val Tyr Tyr Thr
        115                 120                 125

Lys Leu Ser Ser Ser Gly Thr Gln Val Gln Leu Gln Gln Ser Glu Gly
    130                 135                 140

Gly Val Val Gln Pro Gly Arg Ser Leu Arg Leu Ser Cys Ala Ala Ser
145                 150                 155                 160

Gly Phe Thr Phe Ser Ser Tyr Gly Met Asn Trp Val Arg Gln Ala Pro
                165                 170                 175

Gly Lys Gly Leu Glu Trp Val Ser Tyr Ile Ser Ser Ser Ser Ser Thr
            180                 185                 190

Ile Tyr Tyr Ala Asp Ser Val Lys Gly Arg Phe Thr Ile Ser Arg Asp
        195                 200                 205

Asn Ser Lys Asn Thr Leu Tyr Leu Gln Met Asn Ser Leu Arg Ala Glu
    210                 215                 220

Asp Thr Ala Val Tyr Tyr Cys Ala Arg Gly Pro Gly Met Asp Val Trp
225                 230                 235                 240

Gly Gln Gly Thr Thr Val Thr Val Ser Ser
                245                 250

<210> SEQ ID NO 7
<211> LENGTH: 15
<212> TYPE: DNA
<213> ORGANISM: homo sapiens
<220> FEATURE:
<221> NAME/KEY: CDS
<222> LOCATION: (1)..(15)
<223> OTHER INFORMATION: CDR1 region of VH

<400> SEQUENCE: 7 agc tat ggc atg aac                                              15
Ser Tyr Gly Met Asn
1               5

<210> SEQ ID NO 8
<211> LENGTH: 5
<212> TYPE: PRT
<213> ORGANISM: homo sapiens

<400> SEQUENCE: 8

Ser Tyr Gly Met Asn
1               5

<210> SEQ ID NO 9
<211> LENGTH: 51
<212> TYPE: DNA
<213> ORGANISM: homo sapiens
<220> FEATURE:
<221> NAME/KEY: CDS
<222> LOCATION: (1)..(51)
<223> OTHER INFORMATION: CDR2 region of VH

<400> SEQUENCE: 9

```
tac att agt agt agt agt agt acc ata tac tac gca gac tct gtg aag      48
Tyr Ile Ser Ser Ser Ser Ser Thr Ile Tyr Tyr Ala Asp Ser Val Lys
1               5                   10                  15 ggc                                                                   51
Gly
```

<210> SEQ ID NO 10
<211> LENGTH: 17
<212> TYPE: PRT
<213> ORGANISM: homo sapiens

<400> SEQUENCE: 10

Tyr Ile Ser Ser Ser Ser Ser Thr Ile Tyr Tyr Ala Asp Ser Val Lys
1               5                   10                  15

Gly

<210> SEQ ID NO 11
<211> LENGTH: 18
<212> TYPE: DNA
<213> ORGANISM: Homo sapiens
<220> FEATURE:
<221> NAME/KEY: CDS
<222> LOCATION: (1)..(18)
<223> OTHER INFORMATION: CDR3 region of VH

<400> SEQUENCE: 11

```
ggg cct ggt atg gac gtc                                               18
Gly Pro Gly Met Asp Val
1               5
```

<210> SEQ ID NO 12
<211> LENGTH: 6
<212> TYPE: PRT
<213> ORGANISM: Homo sapiens

<400> SEQUENCE: 12

Gly Pro Gly Met Asp Val
1               5

<210> SEQ ID NO 13
<211> LENGTH: 63
<212> TYPE: DNA
<213> ORGANISM: artificial sequence
<220> FEATURE:
<223> OTHER INFORMATION: linker
<220> FEATURE:
<221> NAME/KEY: CDS
<222> LOCATION: (1)..(63)
<223> OTHER INFORMATION: linker VL-VH

<400> SEQUENCE: 13

```
tcc gga ggg tcg acc ata act tcg tat aat gta tac tat acg aag tta      48
Ser Gly Gly Ser Thr Ile Thr Ser Tyr Asn Val Tyr Tyr Thr Lys Leu
1               5                   10                  15
```

```
tcc tcg agc ggt acc                                              63
Ser Ser Ser Gly Thr
            20

<210> SEQ ID NO 14
<211> LENGTH: 21
<212> TYPE: PRT
<213> ORGANISM: artificial sequence
<220> FEATURE:
<223> OTHER INFORMATION: linker

<400> SEQUENCE: 14

Ser Gly Gly Ser Thr Ile Thr Ser Tyr Asn Val Tyr Tyr Thr Lys Leu
1               5                   10                  15

Ser Ser Ser Gly Thr
            20

<210> SEQ ID NO 15
<211> LENGTH: 18
<212> TYPE: PRT
<213> ORGANISM: Homo sapiens
<220> FEATURE:
<221> NAME/KEY: MISC_FEATURE
<223> OTHER INFORMATION: Peptide comprising cleavage site of C5
      convertase. Corresponding to aa 727-744 of mature human protein
      (P01031).

<400> SEQUENCE: 15

Lys Asp Met Gln Leu Gly Arg Leu His Met Lys Thr Leu Leu Pro Val
1               5                   10                  15

Ser Lys

<210> SEQ ID NO 16
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: fibronectin derived peptide

<400> SEQUENCE: 16

Gly Glu Glu Ile Gln Ile Gly His Ile Pro Arg Glu Asp Val Asp Tyr
1               5                   10                  15

His Leu Tyr Pro
            20

<210> SEQ ID NO 17
<211> LENGTH: 34
<212> TYPE: DNA
<213> ORGANISM: Artificial sequence /primer
<220> FEATURE:
<221> NAME/KEY: misc_feature
<222> LOCATION: (1)..(34)
<223> OTHER INFORMATION: PCR primer

<400> SEQUENCE: 17
atccgagtgc acacctgtgg agagaaaggc aaag                            34

<210> SEQ ID NO 18
<211> LENGTH: 34
<212> TYPE: DNA
<213> ORGANISM: Artificial sequence /primer
<220> FEATURE:
<221> NAME/KEY: misc_feature
<222> LOCATION: (1)..(34)
<223> OTHER INFORMATION: PCR primer
```

```
<400> SEQUENCE: 18
tcctcagcgc gcggctctgg tggcagaccg aagg                                  34

<210> SEQ ID NO 19
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: Sequence derived from  AF237583 GenBank acc.
      number

<400> SEQUENCE: 19
caggcggcgc gcgggcagcc ccaggaacca cag                                   33

<210> SEQ ID NO 20
<211> LENGTH: 94
<212> TYPE: DNA
<213> ORGANISM: Homo sapiens
<220> FEATURE:
<221> NAME/KEY: misc_feature
<222> LOCATION: (1)..(94)
<223> OTHER INFORMATION: Sequence derived from  AF237583 GenBank acc.
      number

<400> SEQUENCE: 20
acgtcgatcg cctgctgaat tcttaagtac tatccaggcc cagcagtggg tttgggattg      60
gtttgccact agttttaccc ggggacaggg agag                                  94

<210> SEQ ID NO 21
<211> LENGTH: 41
<212> TYPE: DNA
<213> ORGANISM: Homo sapiens
<220> FEATURE:
<221> NAME/KEY: misc_feature
<222> LOCATION: (1)..(41)
<223> OTHER INFORMATION: Sequence derived from  AF237583 GenBank acc.
      number

<400> SEQUENCE: 21
aggcggcgcg cgacaaaact cacacatgcc caccgtgccc a                          41

<210> SEQ ID NO 22
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: Sequence derived from J00220 GenBank acc.
      number

<400> SEQUENCE: 22
caggcggcgc gcgttccctc aactccacct acc                                   33

<210> SEQ ID NO 23
<211> LENGTH: 32
<212> TYPE: DNA
<213> ORGANISM: Homo sapiens
<220> FEATURE:
<221> NAME/KEY: misc_feature
<222> LOCATION: (1)..(32)
<223> OTHER INFORMATION: Sequence derived from J00220 GenBank acc.
      number

<400> SEQUENCE: 23
```

-continued

```
ccgctactag ttttacccgc caagcggtcg at                                    32

<210> SEQ ID NO 24
<211> LENGTH: 31
<212> TYPE: DNA
<213> ORGANISM: Mus musculus
<220> FEATURE:
<221> NAME/KEY: misc_feature
<222> LOCATION: (1)..(31)
<223> OTHER INFORMATION: Sequence derived from L27437 GenBank acc.
      number

<400> SEQUENCE: 24
caggcggcgc gcggcagacc gaaggctcca c                                     31

<210> SEQ ID NO 25
<211> LENGTH: 32
<212> TYPE: DNA
<213> ORGANISM: Mus musculus
<220> FEATURE:
<221> NAME/KEY: misc_feature
<222> LOCATION: (1)..(32)
<223> OTHER INFORMATION: Sequence derived from J00220 GenBank acc.
      number

<400> SEQUENCE: 25
ccgctactag ttttaccagg agagtgggag ag                                    32

<210> SEQ ID NO 26
<211> LENGTH: 36
<212> TYPE: DNA
<213> ORGANISM: Mus musculus
<220> FEATURE:
<221> NAME/KEY: misc_feature
<222> LOCATION: (1)..(36)
<223> OTHER INFORMATION: Sequence derived from L27437 GenBank acc.
      number

<400> SEQUENCE: 26
caggcggcgc gcggttgtaa gccttgcata tgtaca                                36

<210> SEQ ID NO 27
<211> LENGTH: 33
<212> TYPE: DNA
<213> ORGANISM: Rattus norvegicus
<220> FEATURE:
<221> NAME/KEY: misc_feature
<222> LOCATION: (1)..(33)
<223> OTHER INFORMATION: Sequence derived from M28671 GenBank acc.
      number

<400> SEQUENCE: 27
caggcggcgc gcgggctagt cagaaaacca cag                                   33

<210> SEQ ID NO 28
<211> LENGTH: 33
<212> TYPE: DNA
<213> ORGANISM: Rattus norvegicus
<220> FEATURE:
<221> NAME/KEY: misc_feature
<222> LOCATION: (1)..(33)
<223> OTHER INFORMATION: Sequence derived from M28671 GenBank acc.
      number

<400> SEQUENCE: 28
ccgctactag ttttacccgg aggccgggag atg                                   33

<210> SEQ ID NO 29
<211> LENGTH: 33
```

```
<212> TYPE: DNA
<213> ORGANISM: Rattus norvegicus
<220> FEATURE:
<221> NAME/KEY: misc_feature
<222> LOCATION: (1)..(33)
<223> OTHER INFORMATION: Sequence derived from M28671 GenBank acc.
      number

<400> SEQUENCE: 29
caggcggcgc gccacaaatg ccctacatgc cct                                    33

<210> SEQ ID NO 30
<211> LENGTH: 35
<212> TYPE: DNA
<213> ORGANISM: Homo sapiens
<220> FEATURE:
<221> NAME/KEY: misc_feature
<222> LOCATION: (1)..(35)
<223> OTHER INFORMATION: Universal oligonucleotide for VL1
      amplification.

<400> SEQUENCE: 30
caggtgtgca ctcggacatc crgdtgaccc agtct                                  35

<210> SEQ ID NO 31
<211> LENGTH: 35
<212> TYPE: DNA
<213> ORGANISM: Homo sapiens
<220> FEATURE:
<221> NAME/KEY: misc_feature
<222> LOCATION: (1)..(35)
<223> OTHER INFORMATION: nucleotide in position 29 is "n"
      Universal oligonucleotide for VL2 amplification.

<400> SEQUENCE: 31
caggtgtgca ctcggatatt gtgwtgacac agwct                                  35

<210> SEQ ID NO 32
<211> LENGTH: 31
<212> TYPE: DNA
<213> ORGANISM: Homo sapiens
<220> FEATURE:
<221> NAME/KEY: misc_feature
<222> LOCATION: (1)..(31)
<223> OTHER INFORMATION: Universal oligonucleotide for VL3
      amplification.

<400> SEQUENCE: 32
caggtgtgca ctcgcagcct gtgctgcary c                                      31

<210> SEQ ID NO 33
<211> LENGTH: 35
<212> TYPE: DNA
<213> ORGANISM: Homo sapiens
<220> FEATURE:
<221> NAME/KEY: misc_feature
<222> LOCATION: (1)..(35)
<223> OTHER INFORMATION: Universal oligonucleotide for VL4
      amplification.

<400> SEQUENCE: 33
caggtgtgca ctcgtcctat gwgctgacwc agcca                                  35

<210> SEQ ID NO 34
<211> LENGTH: 29
<212> TYPE: DNA
<213> ORGANISM: Homo sapiens
<220> FEATURE:
<221> NAME/KEY: misc_feature
<222> LOCATION: (1)..(29)
```

```
<223> OTHER INFORMATION: Universal oligonucleotide for JH1
      amplification.

<400> SEQUENCE: 34
gacccgcgcg cggagacrgt gaccagggt                                    29

<210> SEQ ID NO 35
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: Universal oligonucleotide for JH2
      amplification.

<400> SEQUENCE: 35
gacccgcgcg cagagacggt gaccrtkgt                                    29
```

ANTI-C5 ALPHA ANTIBODIES

This application is a U.S. national stage application under 35 U.S.C. §371 of PCT/EP2003/007487, filed Jul. 10, 2003, which claims priority from Italian application number MI2002A001527, filed Jul. 11, 2002.

This application includes a "Sequence Listing," which is provided as an electronic document on a compact disc (CD-R). This compact disc contains the file "Substitute Sequence Listing.txt" (24 kilobytes, created on Sep. 24, 2010), which is hereby incorporated by reference in its entirety.

FIELD OF THE INVENTION AND BACKGROUND OF THE ART

Activation of the complement system (C system) represents an important mechanism in the immune defence. At the same time it represents a double-edged weapon because on the one hand guarantees protection of the host but on the other is capable of damaging tissues where complement is activated by several pathological circumstances. The increased susceptibility to bacterial infections and autoimmune disorders observed in patients with inherited deficiencies of the C system clearly demonstrates the particular importance of this system in host protection against infectious agents and in the clearance of immunocomplexes.

These protective functions result from complement activation in cascade fashion that generates biologically active products. Some of those, such as C1q, C3b and C3bi, opsonize the infectious agents enabling their disposal. Instead others, such as C5a and C5b67, have the function to recruit phagocytic cells at the site of inflammation or lyse sensitive targets as in the case of the membrane attack complex (MAC). Unfortunately these molecules, once they are produced, are not able to discriminate between endogenous and exogenous targets, and would provoke serious damage to tissues and cells if those were not protected by potent membrane or extracellular inhibitors acting at various levels in the complement activation cascade. However, the action of inhibitors is overwhelmed in presence of a massive activation of the C system, in serious infectious diseases or autoimmune disorders, and the activated complement causes tissue and cell destruction.

The C5a fragment and the C terminal complex (TCC) are among the products involved in tissue destruction in several inflammatory processes. Above normal levels of these activation products can be found in synovial fluid of rheumatoid arthritis patients and in cerebrospinal fluid of patients with several diseases of the central nervous system. Elevated C5a levels have been found also in polytraumatised patients as well as in patients with damage from myocardial ischaemia and re-perfusion.

Therefore the role of C5a in development of these diseases is now recognised.

This is demonstrated by the signs of pulmonary stress, hypotension and leukopenia shown by animals that have received intravenous injection of this anaphylatoxin. Moreover bronchial instillation of C5a is capable of inducing strong inflammatory reactions in rabbit lung.

TCC is generated from the C5b fragment released by enzymatic cleavage of C5 by the action of C5 convertase. Recently it has been demonstrated that TCC induces inflammation because of tissue damage deriving from its lytic activity and of numerous non-cytotoxic effects on phagocytes and other cell types.

TCC has been identified in several tissues in diverse pathological conditions, including rheumatoid arthritis, glomerulopathies multiple sclerosis, demyelinating peripheral neuropathies, atherosclerosis and myocardial infarction. The development of experimental animal models of these diseases with selective deficiencies in late C components has further contributed to define the role of these components in development of tissue damage.

Because of the fundamental role played by C5a and TCC in promoting chronic inflammation and tissue damage, several attempts have been made to neutralise the late components of the C complex as therapeutic strategy to prevent these complications in diseases associated with C5 activation. This molecule turns out to be an ideal therapeutic target, since its neutralisation inhibits the late sequence of activation events of the cascade, without interfering with the opsonizing activity of the early components of this cascade. Mouse monoclonal antibodies specific for human, mouse and rat C5 and capable of inhibiting the production of C5a and of the membrane attack complex (MAC) are already commercially available. Anti-C5 antibodies have been successfully used in mice to prevent the development of collagen-induced arthritis and to improve the clinical curse of glomerulonephritis, and in rats to reduce myocardial ischemia and re-perfusion.

In the last years two single chain antibodies (single chain antibody or single chain fragment variable, scFv) have been produced that are both described in patent application WO 95/29697. These antibodies are able to penetrate tissues more rapidly than the whole antibody. The first single chain antibody obtained by assembling variable regions of a mouse antibody for C5 retains the ability of the original antibody to inhibit assembly of the MAC and partially block C5a production (Evans, M. J et al, 1995, Mol. Immunol. 32:1183). Moreover, this antibody is able to prevent C5b-9 deposits in the heart re-perfused with human plasma or in heart insufficiency. The second scFv is a humanised mouse antibody anti-C5, that is obtained by inserting murine CDR regions (complementarity determining region) in the structure of the variable region of human light and heavy chains. This antibody (Thomas, T. C. et al., 1996, Mol. Immunol. 33:1389) is able to inhibit C5a and C5b-9 formation although the recognised epitope mapped around amino acids 860-865 of the C5 molecule and corresponding to peptide KSSKC [SEQ ID NO: 36], turns out to be far from the C5 convertase cleavage site. Moreover subsequent studies (Fitch, J. C. et al., 1999, Circulation 100:2499) have demonstrated that this antibody is able to inhibit complement hemolytic activity, to attenuate myocardial damage, cognitive damage and postoperative haemorrhage in a group of patients with cardiopulmonary bypass.

SUMMARY

The main aspect of the invention refers to an antibody of human origin specific for the C5 component of activated complement and characterised by the fact that it inhibits cleavage of the C5 alpha chain into C5a and C5b. In particular, the antibody is recombinant and recognises an epitope comprising the proteolytic site for the C5 convertase on the alpha chain of the C5 complement component.

According to a preferred embodiment, the recombinant antibody is composed of a single chain (scFv) comprising a variable region of the light chain covalently bound to a variable region of the heavy chain and, according to an even more preferred aspect is composed of or comprises at least one of amino acid sequences selected among SEQ ID NO: 2, 4, 6 or proteins having at least 95% homology to such polypeptides.

In accordance with a further aspect, the invention includes the isolated nucleotide sequences encoding antibodies specific for C5 component of activated complement. These antibodies are characterised by the fact that they inhibit cleavage of the C5 alpha chain into C5a and C5b, and in particular the sequences chosen between: SEQ ID NO: 1 or 3 or 5 and the vectors containing these sequences. In accordance with a further aspect, the invention refers to the therapeutic use of antibodies and nucleotide sequences for preparation of drugs that prevent and treat diseases involving uncontrolled activation of the complement system, in particular: rheumatoid, arthritis, glomerulonephrits, multiple sclerosis, demyelinating peripheral neuropathies, atherosclerosis.

DESCRIPTION OF THE FIGURES

Panel A) The ELISA assay measures the amount of C5a fragment released in the supernatant after enzymatic cleavage of C5, using antibodies anti-C5 as described in example 6. Incubation of C5 with antibodies Ts-a12 and Ts-a12/22 of the invention inhibits formation of the C5a fragment. Sheep erythrocytes sensitised with antibodies and coated until the C3b (EAC1-3b) complement step were added to the mixture of TS-A12 or TS-A12/22 and C5, and the mixture was further incubated for 30 minutes at 37° C. (panel B). As shown in FIGS. 1A and B, TS-A12 and TS-A12/22 antibodies inhibit C5 cleavage by C5 convertase and therefore inhibit formation of C5a (Panel A) and of TCC (Panel B).

Symbols: -▲-: Ts-A12/22; -■-: unrelated scFv; -◇-: TS-A12.

Figure 2:
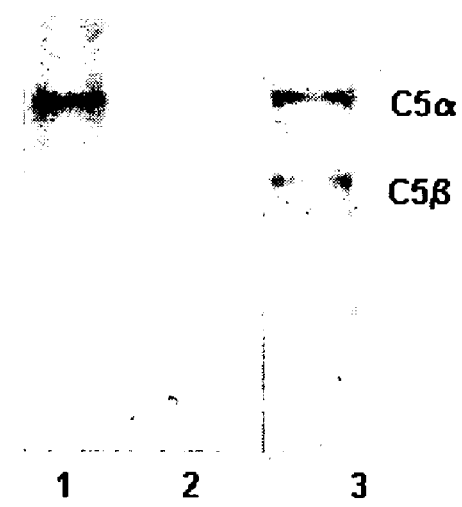

FIG. 2. Immunoblotting to identify the C5 chain recognised by scFv TSA-12/22.

The alpha and beta chains of C5 were electrophoretically separated by means of SDS-PAGE in 10% polyacrylamide and then transferred onto nitrocellulose. The immunoblot (lanes 1 and 2) was developed with TSA-12/22 antibody and revealed by incubation with anti-SV5 (SV5 tag) monoclonal antibody followed by incubation with a goat anti-mouse IgG antibody labeled with alkaline phosphatase. Lane 1: 100 ng of C5 alpha chain; lane 2: 100 ng of beta chain; lane 3: mixture of the two chains. Immunoblot in lane 3, used as positive control, was developed with a biotin conjugated goat anti-human C5 antibody that recognises both alpha and beta chains and was revealed with alkaline phosphatase labeled avidin. It can be seen that scFv TSA-12/22 recognises the alpha chain of C5 in lane 1, but not the beta chain in lane 2.

Figure 3:
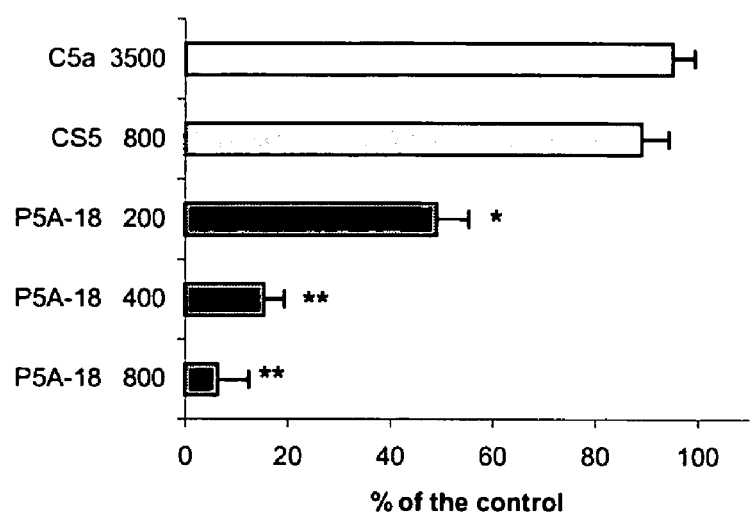

FIG. 3. Inhibition of the binding of C5 and scFv of the invention by peptide P5A-18 (KDMQLGRLHMKTLL-PVSK) (SEQ ID NO:15) comprising the C5 convertase cleavage site.

Mixtures of scFv TSA-12/22 (1 µg/ml) containing 200, 400 and 800 ng of P5A-18 peptide, with sequence KDMQLGR-LHMKTLLPVSK [SEQ ID NO:15], comprising the C5 convertase cleavage site, or 800 ng of unrelated peptide CS5, derived from fibronectin (GEEIQIGHIPREDVDYHLYP SEQ ID No. 16 of sequence listing) or 3.5 µg of C5a fragment or saline solution (control) were incubated as described in example 8. Binding of the antibody, pre-incubated in different conditions, was assessed by immuno-enzymatic assay using C5 on solid phase. Inhibition by the P5A-18 peptide of the binding between scFv of the invention and C5 is dose-dependent, ranging between 45% to 90% for peptide concentrations of 200 and 800 ng, respectively. These values correspond to a Ki of 1 µM for the P5A-18 peptide. No inhibition is observed using C5A or the unrelated peptide.

Figure 4:
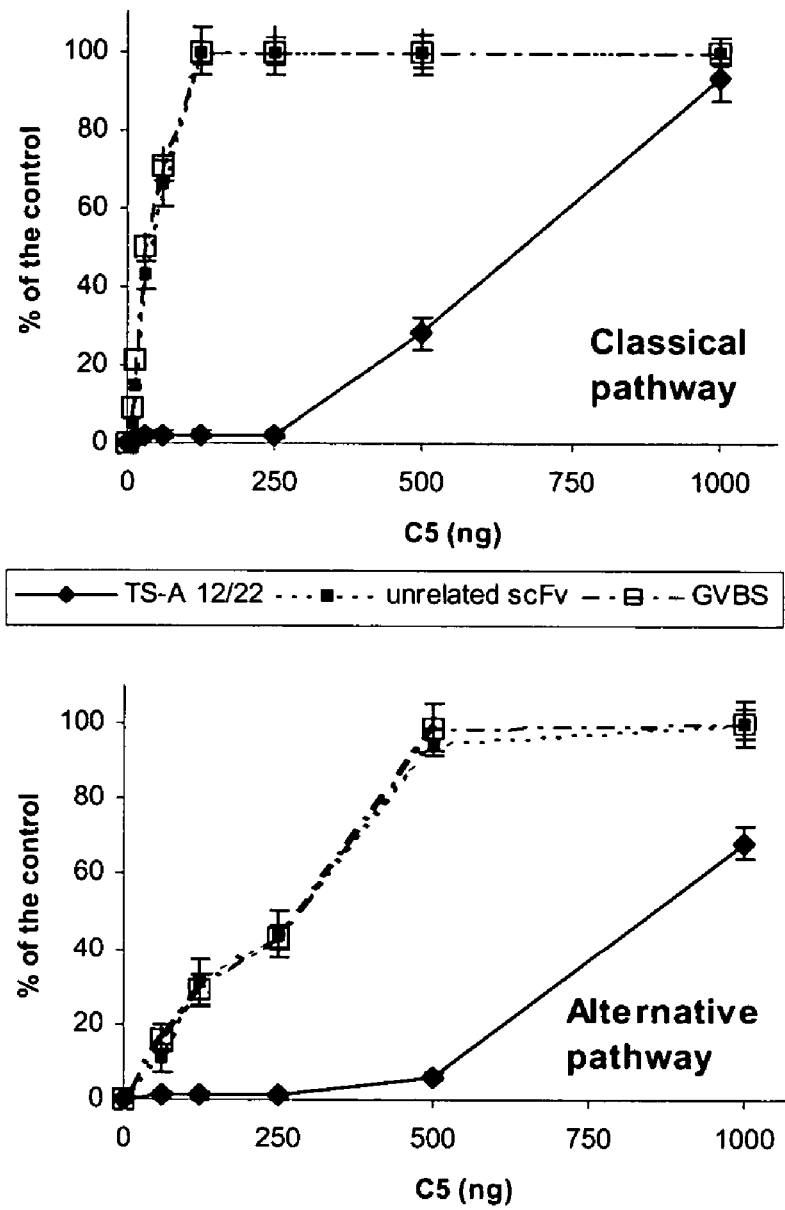

FIG. 4. Inhibition of hemolytic activity of C5 by the TS-A12/22 antibody.

Values from spectrophotometric reading performed at 412 nm to measure inhibition of lysis of sheep erythrocytes coated with EAC1-3b, through the classical complement activation pathway (A Panel); or of rabbit erythrocytes in order to measure the alternative pathway of complement activation (B Panel). Increasing amounts of C5 were mixed with 600 ng of the scFv antibody of the invention with an unrelated scFv, or with GVBS in which the scFv of the invention were solubilised, as described in example 9. After incubation with serum lacking in C5, obtained from a patient with selective deficiency of this complement component, the percentage of hemolysis was measured compared to the 100% value obtained by lysing erythrocytes in an equal volume of distilled $H_2O$ and a blank obtained by resuspending eythrocytes in GBVS.

Symbols: -◇-: TS-A12/22; -■-: unrelated scFv; -▲-: GVBS.

Figure 5:
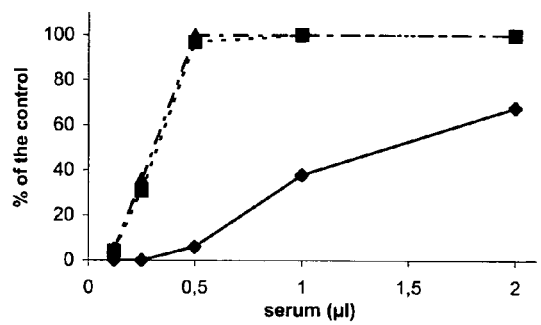
Figure 5:
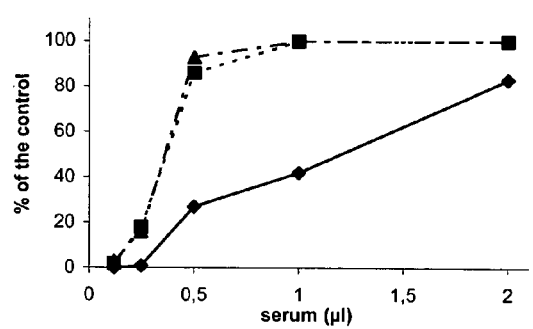
Figure 5:
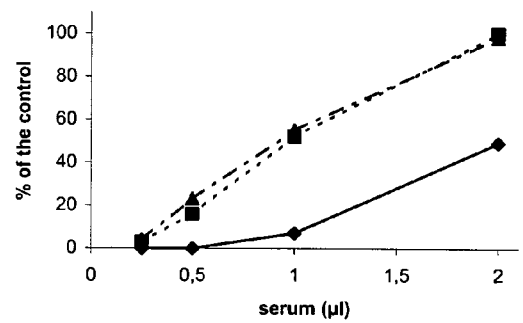
Figure 5:
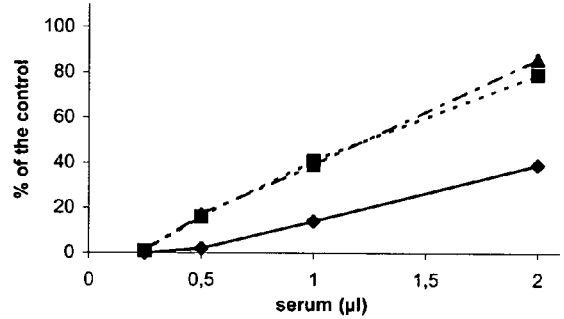

FIG. 5. Inhibition of C5 hemolytic activity in mammalian serum by the TS-A12/22 antibody.

Measurements were performed as described in example 8, using sera from human (panel A), rat (panel B), rabbit (panel C), mouse (panel D).

Symbols: -▲-: GVBS TS-A12/22; -■-: unrelated scFv; -◇-: TS-A12/22.

Figure 6:
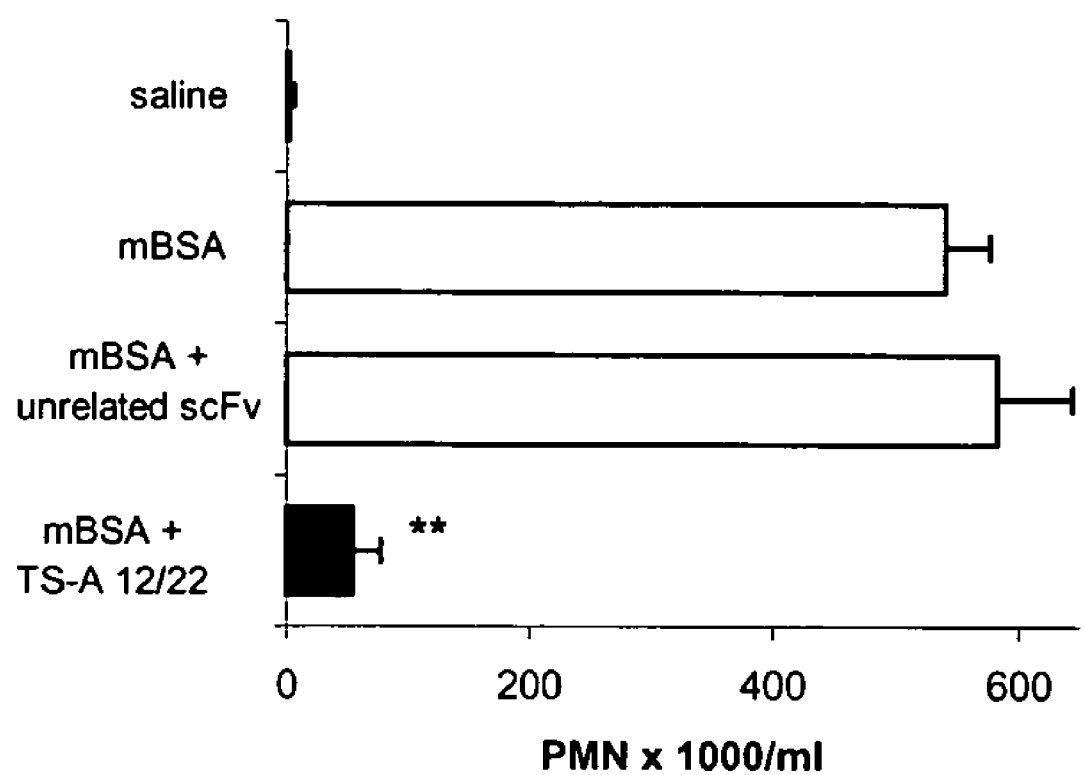

FIG. 6. Inhibition of intra-articular migration of Polymorphonuclear Leukocytes (PMN) by the TS-A12/22 antibody in rat models of antigen-induced arthritis.

Polymorphonuclear Leukocytes (PMN), isolated from intra-articular wash out of rats with arthritis induced by instillation of BSA (mBSA), were incubated with antibody TS-A12/22 or with an unrelated antibody, as described in example 10. The number of PMN in the joint treated with the antibody of the invention appears drastically reduced.

Saline solution: control without induced arthritis; mBSA: BSA-induced arthritis, untreated; unrelated: BSA-induced arthritis, treated with unrelated scFv antibody; Ts-a12/22: BSA-induced arthritis, treated with the antibody of the invention.

Figure 7:
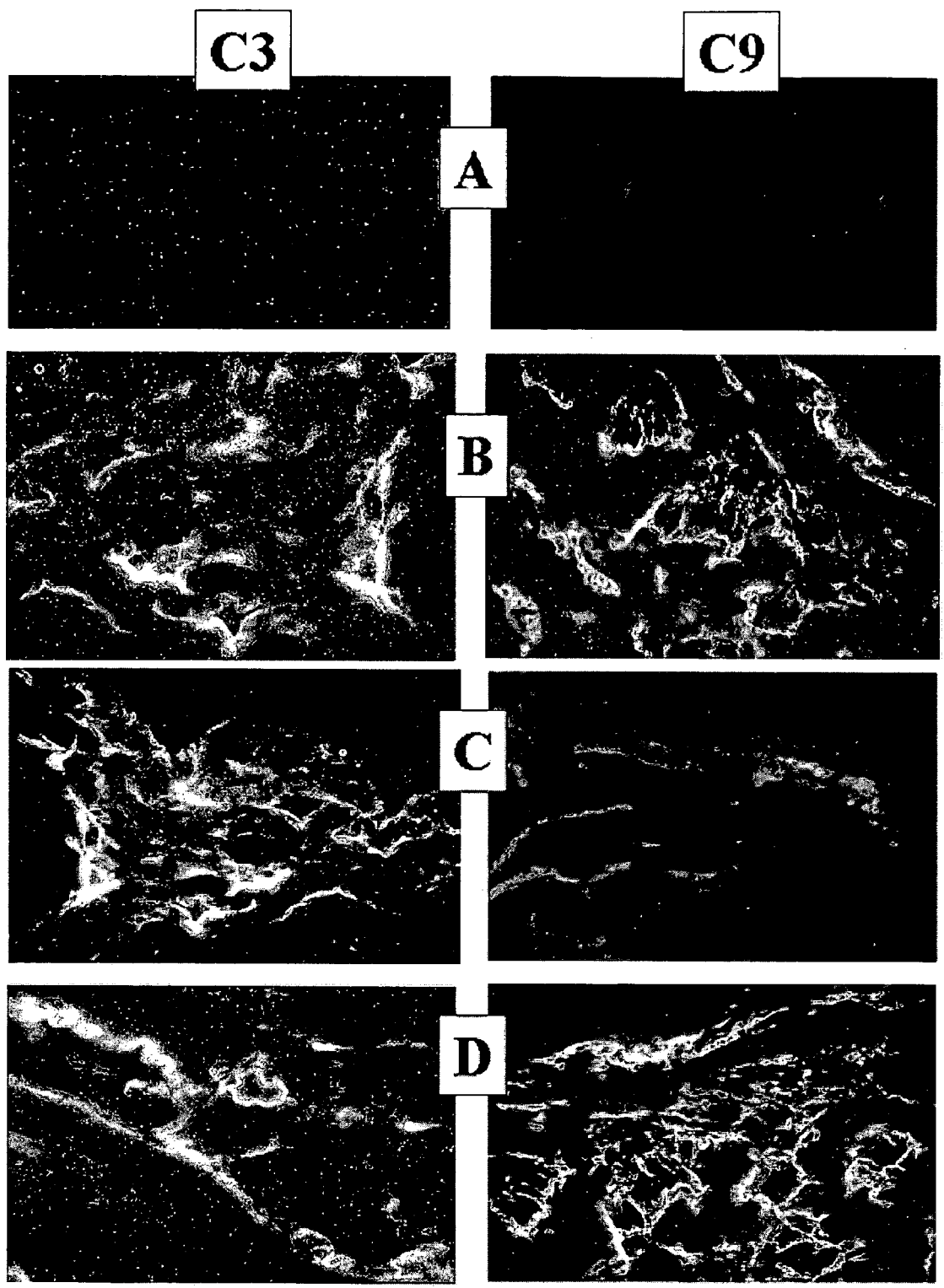

FIG. 7. Immunofluorescence analysis of synovial membrane from rats with antigen-induced arthritis.

Histological sections of joints from rats treated with intra-articular injection of saline (A), BSA (B), BSA with TS-A12/22 (C) and BSA with the unrelated antibody (D) were analysed by immunofluorescence for the presence of complement components C3 and C9, as described in example 10. It is emphasised that the treatment with TS-A12/22 does not affect the deposition of C3 but significantly reduces that of C9, thus confirming the inhibition of C5.

Figure 8:
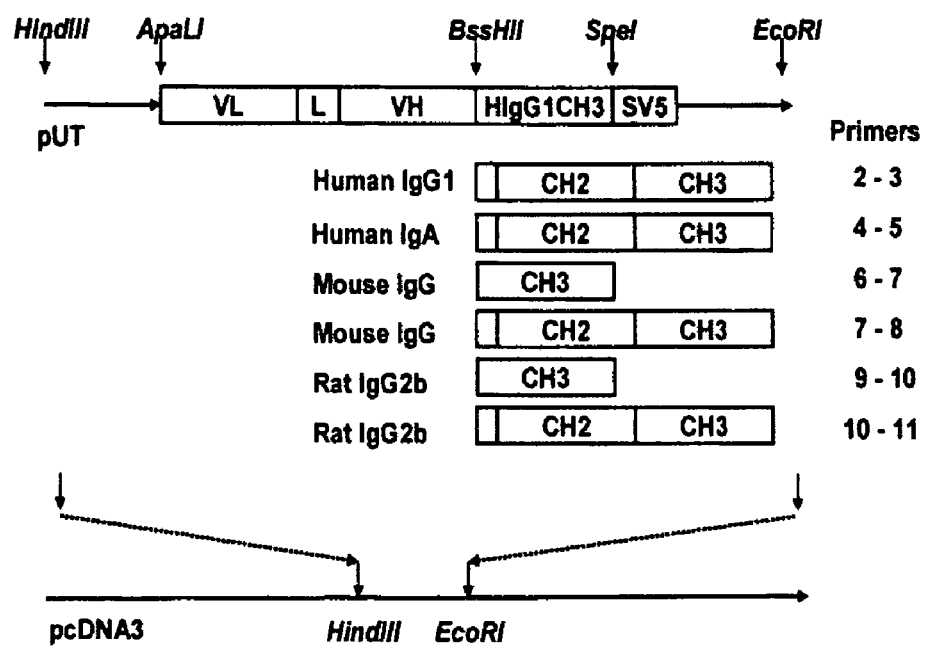

FIG. 8. Schematic representation of minibodies prepared from ScFv sequences including human, mouse and rat constant regions.

Figure 9:
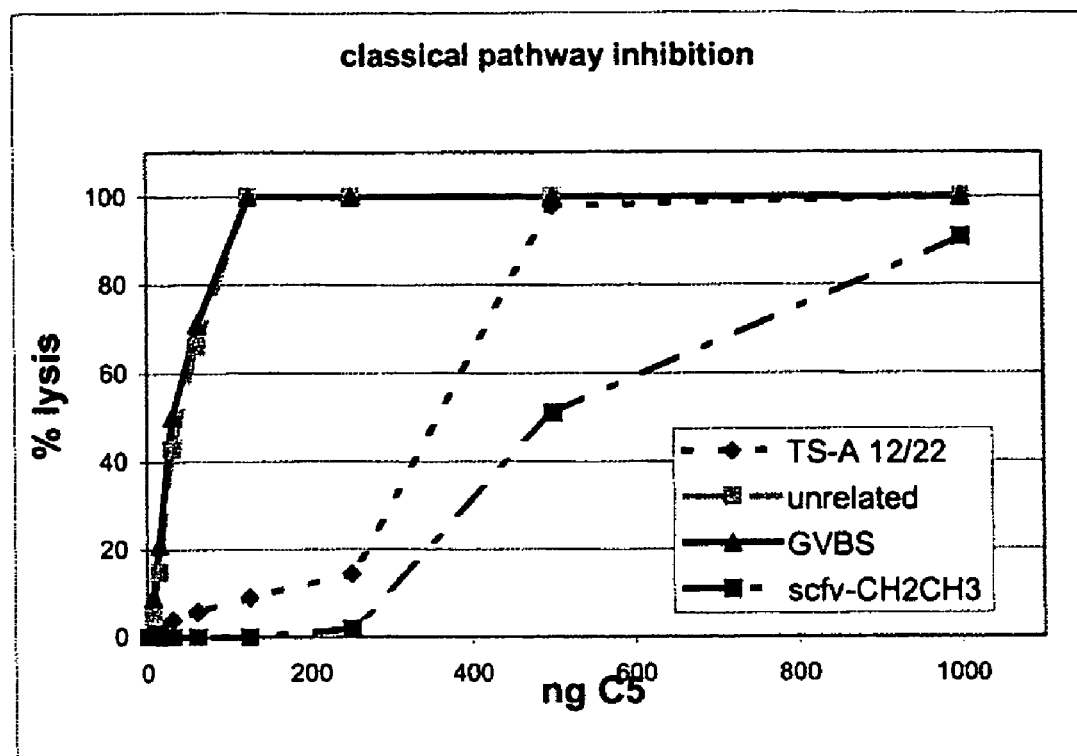

FIG. 9. Inhibition of the classical complement activation pathway.

Symbols: -▲-: GVBS; -■-: unrelated scFv; -◇-: TS-A12/22-CH2CH3 (minibody); -■-TS-A12/22 (scFv).

Figure 10:
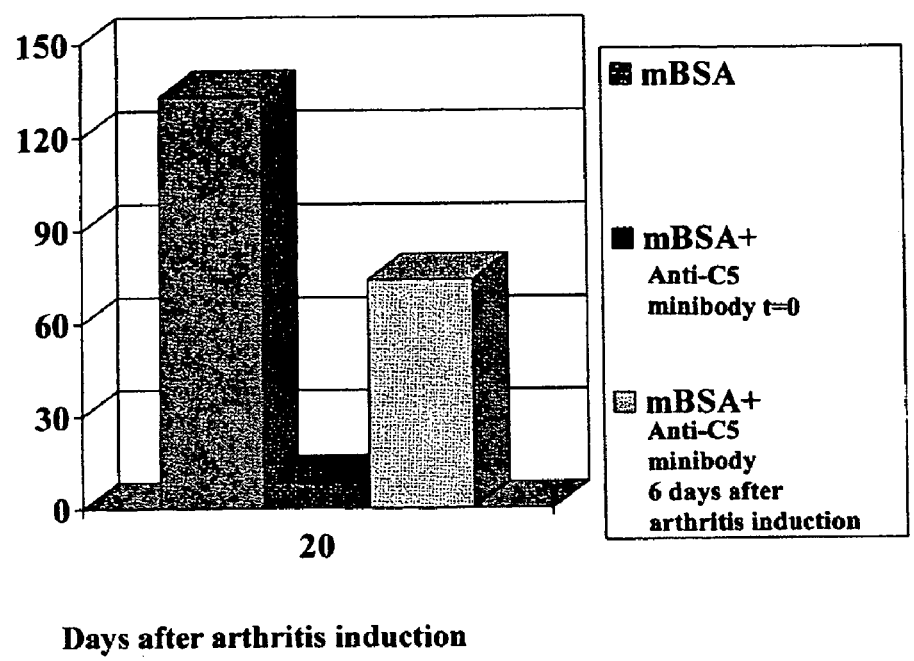

FIG. 10. Inhibition of intra-articular migration of Polymorphonuclear Leukocytes (PMN) by the TS-A12/22-CH2CH3 antibody (minibody) in rat models of antigen-induced arthritis.

From left: bar 1: control (mBSA); bar 2: mBSA+TS-A12/22-CH2CH3 (minibody) injected at time 0; bar 3: mBSA+TS-A12/22-CH2CH3 (minibody) injected at 6 hours from induction of arthritis.

Figure 11:
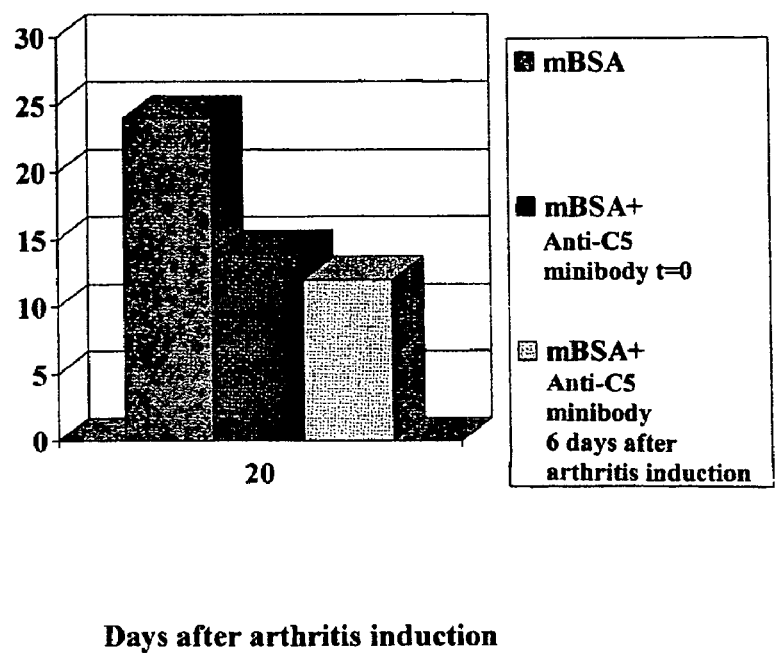

FIG. 11. Reduction of the joint swelling.

The antibody, under the form of minibody, was injected in the model of mBSA-induced arthritis in rat at time 0 and 6 days after BSA treatment. Percentage values on the ordinate have been obtained with respect to the basal diameter of the joint prior to induction of arthritis. Days are indicated on the abscissa.

From left: bar 1: control (mBSA); bar 2: mBSA+TS-A12/22-CH2CH3 (minibody) injected at time 0 from induction of arthritis; bar 3: mBSA+TS-A12/22-CH2CH3 (minibody) injected at 6 hours from induction of arthritis.

DETAILED DESCRIPTION OF THE INVENTION

The main object of the present invention relates to an antibody of human origin which has specificity for the C5 component of the complement system and is characterised by the fact of inhibiting the cleavage of C5 alpha chain, also termed activated C5, into C5a and C5b fragments. This cleavage occurs as result of complement activation occurring by known mechanisms.

Following Complement activation, a C5 convertase is produced which cleaves the alpha chain of factor C5 generating a fragment of approximately 70 amino acids (aa), known as C5a, and a C-terminal fragment of 925 aa, C5b. The products resulting from C5 activation, C5a and C5b, are biologically active. In particular, C5a has chemotactic activity toward polymorphonuclear leukocytes and monocytes, whereas the C5b fragment contributes to formation of the terminal complement complex (TCC).

The antibody is preferably recombinant.

The antibody of the invention is of human origin, i.e. it is entirely derived from an antibody repertoire obtained from human lymphocytes. These antibodies have both framework and antigen complementary regions (CDR) of human origin, unlike humanised antibodies where only the framework is of human origin, while the CDR are of murine origin.

Herein, by recombinant antibody it is meant an antibody composed of at least one variable region derived from the heavy or light chain of an immunoglobulin and produced by means of genetic engineering techniques from the nucleotide sequences coding the characterising regions of the antibody. The recombinant antibody is produced in a host organism which is usually a bacteria, a yeast, or a higher eukaryotic cell (of plant or animal origin). The technique of genetic engineering allows to produce entirely human antibodies or to select a format different from natural antibodies. On the contrary, antibodies produced by the classical hybridoma technology described by Milstein et al., can be only from mouse or rat and have the typical Y shaped format of four-chain antibodies. The four chains, identical pair-wise, comprise a heavy and a light chain, each consisting of a constant and variable region, as described by Rathburn, G. et al. (1989) in Immunoglobulin genes, Academic Press, New York.

According to a preferred embodiment, the anti-C5 recombinant antibody of the invention is characterised by the fact of recognising an epitope on the alpha chain of the C5 component, which comprises the cleavage region of C5 convertase. The binding specificity of the antibody of the invention for the epitope comprising the cleavage site for C5 convertase, which is positioned between glycine 733 and arginine 734 of human C5 according to the SwissProt Data Base numbering for human C5 (SEQ ID P01031), can be verified in vitro. For instance, it can be verified by means of an ELISA competition assay on C5 that makes use of a synthetic peptide, as for example the peptide KDMQLGR↓LHMKTLLPVSK (SEQ ID NO:15) (where the arrow indicates the proteolytic cleavage site), corresponding to the region 727-744 of the human mature protein. According to this aspect, the antibody is preferably characterised by the ability of recognising a region with at least 80%, preferably at least 90% 95% homology to the peptide KDMQLGR↓LHMKTLLPVSK (corresponding to the SEQ ID NO:15). More preferably it recognises an epitope of at least 6-10 amino acids composed of 1-5 amino acids upstream and 1-5 amino acids downstream the peptide bond cleaved by the enzyme C5 convertase, preferably the epitope is LGRLHM (SEQ ID NO:37). The region surrounding the cleavage site is highly conserved across several mammalian species, therefore the antibody of the invention recognises with very similar binding efficiency the C5 molecule of rat, mouse, rabbit etc. Moreover the antibody has in each animal species the same effect to block the conversion of activated C5 into its active fragments C5a+C5b.

The recombinant antibody of the invention is preferably in a single chain form (scFv), even more preferably it corresponds to SEQ ID NO:6, and comprises the variable region of the light chain covalently joined to the variable region of the heavy chain, either directly or via an amino acid sequence termed linker. Herein by scFv it is meant a single polypeptide chain antibody, composed of the variable region of the light chain joined to the variable region of the heavy chain either directly or via synthetic linker. Linkers composed of non-natural amino acid sequences (synthetic) are known in the art and are described for instance in (1999): Combinatorial Chemistry and Technology: Principles, Methods, and application, Marcel Dekker Inc, NY USA. The synthetic linker is preferably the nucleotide sequence SEQ ID NO:13 of the Sequence Listing.

In the scFv antibody of the invention, VH and VL chains are preferably in the order VL-VH from the N— to the C-terminus of the polypeptide chain. This format, in which the N-terminal consists of VL chain, confers greater hydrophilicity to the whole protein expressed as such and to fusion proteins comprising both VL and VH regions. Furthermore it makes possible the upstream or downstream insertion of peptide sequences termed "tag" or "flag", which do not alter the binding characteristics but are used for instance to facilitate the immunological detection of the antibody, or its production or purification. For the purpose of the present invention, the antibody may also consist of the format (N—C terminus) VH-VL, or it may contain only one of the two variable chains, preferably the VH chain corresponding to SEQ ID NO:4, also in association with different VL chains, also independently of their specificity, as for instance selectable through interaction of the VH chain corresponding to SEQ ID NO:4 with "collections of molecular repertoires".

In the antibody of the invention, the VL chain has a sequence preferably corresponding to SEQ ID NO:2 that could be covalently linked to a VH chain which preferably corresponds to SEQ ID NO:4.

In the scFv antibody, preferably at least the VH chain has the above indicated anti-C5 specificity and preferably corresponds to SEQ ID NO:4 of the Sequence Listing or to the isotypic variants or conservative mutations of this sequence. Therefore, according to this aspect, the invention comprises all polypeptides comprising a region having at least 95% homology, preferably 98% or 99% homology with the amino acid sequence of the VH region, preferably VH3 corresponding to SEQ ID NO:4. A particularly preferred embodiment of this scFv is represented by the antibody having amino acid sequence corresponding to SEQ ID NO:6, which corresponds to sequence 4 and 2 joined by a linker peptide to a sequence corresponding to SEQ ID NO:14. In accordance with a particularly preferred embodiment the scFv antibody corresponding to the SEQ ID NO:6, has an equilibrium constant for the antigen higher than $1 \times 10^7$, preferably higher than $1 \times 10^8$.

In a preferred embodiment, the nucleotide sequence of scFv antibody is used to engineer expression cassettes for recombinant antibodies comprising the constant region of immunoglobulin heavy chains, preferably IgG, even more preferably of human, mouse or rat origin. Even more preferably these constructs comprise CH2 and CH3 regions either individually or in association. The expression cassettes made according to this procedure are cloned in suitable expression vectors which are used for transfection of eukaryotic cells, preferably of mammalian origin, as for instance HEK293, CHO, COS-1 BHK, myeloma cells or other cells suitable for expression of these protein products. According to a particularly preferred embodiment, the scFv antibody corresponding to SEQ ID NO:5 is produced in recombinant form with rat CH2 and CH3 sequences. In this form, the recombinant antibody dimerizes and a dimeric scFv TSA22-12 represents a particularly preferred embodiment of the invention.

Anyway are enclosed in this scope of the present invention the amino-acid sequences obtained by mutation of the sequences contained in the annexed Sequence Listing, as long as these mutations do not alter the described anti-C5 antibody specificity. The mutation can be "conservative", when it is based on an amino-acid with similar structural or chemical characteristics with respect to polarity, charge, solubility, hydrophobicity, hydrophilicity or it is based on the amphipathic nature of the amino-acid residues involved. For instance groups of amino acids sharing similar characteristics of polarity are composed by non-polar (hydrophobic) aa which include alanine, leucine, isoleucine, valine, proline, phenylalanine, tryptophan and methionine; non-polar or neutral amino acids that include: glycine, serine, threonine, cysteine, tyrosine, asparagine and glutamine; positively charged (basic) amino acids that include: arginine, lysine and histidine; and the group of negatively charged (acidic) amino acids that comprises: aspartic acid and glutamic acid. Mutations also can be produced randomly, for instance using DNA polymerases known to be "error prone". Therefore, according to a further aspect, this invention comprises recombinant antibodies generated by mutagenesis of nucleotide sequences SEQ ID NO:3 and 5 corresponding to sequences coding the VH region and for antibody in the scFv form. In accordance with this aspect, the invention therefore includes a procedure to generate antibodies with specificity for the C5 component of activated complement which may have or not have the ability to block cleavage of C5 alpha in its biologically active components. This procedure essentially includes the use of any one of the sequences SEQ ID NO:4 or SEQ ID NO:6 or preferably the random or site directed mutagenesis of the nucleotide sequences encoding for SEQ ID NO:4 and NO:6. Therefore this procedure preferably includes mutagenesis of the nucleotide sequences SEQ ID NO:3 and SEQ ID NO:5.

Within the preferred format of the antibody, consisting of variable regions of antibody light or heavy chain fused in a single scFv chain via a protein linker, the light chain is more preferably the lambda chain, and in particular the Vλ3/V2-14 chain, or the kappa chain, preferably the Vκ4/DPK24. The heavy chain is the VH3 chain, in particular the VH3/V-48, as defined in the Vbase index. According to this aspect the invention comprises all the antibodies derived by mutagenesis of the nucleotide sequence coding the VH chain or the scFv of the invention. These antibodies are characterized by the fact that they retain specificity for the C5 component of the complement system and of inhibiting cleavage of the C5 alpha chain, also termed activated C5, into C5a and C5b fragments.

It is known to the skilled person that the antigen binding specificity of an antibody is mainly determined by the CDR regions (Complementarity Determining Region) which are defined as hyper-variable regions of the antibody. Three hyper-variable regions for each variable region exist in both the heavy and the light chain. However, not unanimously accepted are the precise boundaries of the less variable or "framework" regions within which the CDR are comprised. Indeed two different classifications exist. The first is based on "sequence variability" (Kabat et al.), while the second is based on "structural variability" (Chothia et al.). However, because the antigen binding specificity is mainly due to the CDR regions, it has been possible, by using DNA recombinant techniques, to engineer chimeric antibodies that exploit the binding specificity of murine CDR mounted on the framework regions of human antibodies. The specificity of such antibodies turns out to be the same as for the murine antibody. The present invention is composed of amino acid and nucleotide sequences of the 3 CDR regions of the variable part of the light chain and of the 3 CDR regions of the variable part of the heavy chains (SEQ ID NO:7, 8, 9 respectively). Therefore are included in the range of the particular embodiment of the present invention all antibodies generated by "grafting" the CDR regions or at least the third CDR, corresponding to the SEQ ID NO:9, in other antibody support structure or in antibody-like support structures. Examples of the latter are "minibodies" in which the CDR of the invention are three-dimensionally positioned in a way to maintain C5 binding specificity.

In agreement with this aspect, the present invention comprises in the essence, whichever recombinant human antibody able to recognise the epitope comprising the cleavage region of C5 convertase on activated factor C5. The recombinant human antibody is preferably characterised by the fact that it comprises as CDR regions at least three of the amino acid sequences identified in the sequence listing, like: SEQ ID NO:7, SEQ ID NO:8, SEQ ID NO:9 or their conservative mutations.

Moreover the invention includes chimeric proteins comprising at least one of the polypeptides corresponding to the SEQ ID NO:2, 4, or 6 or those, obtainable by means of genetic engineering techniques, carrying conservative or non-conservative mutations and at least 95%, more preferably 98% or even 99% homologous to the original sequences. Therefore the invention extends to polypeptides comprising at least one of the antibody-specific amino acid sequences defined as SEQ ID NO:2, 4, 6, 8, 10, 12, also when those are prepared in a form that differs from the canonical or natural form of antibodies. Also comprised in the present invention are embodiments of chimeric immunoglobulin comprising at least one of the amino acid sequences identified as SEQ ID NO:2, 4 or 6 or functional domains derived from such sequences in combination with the amino acid sequence of Ig (immunoglobulin) heavy chain constant regions or subdomains of these regions (i.e. $CH_2$ or $CH_3$ domains) derived for example from amino acid (aa) sequences known in the database (i.e. human Ig A heavy chain gene of 00220, human Ig G heavy chain gene AF 237583, *Mus musculus* L274371 g gamma heavy chain, *Rattus norvegicus* heavy chain region M28671). Preferably the antibody is dimeric. The invention also comprises sequences selected among SEQ ID NO:2, 4 or 6, when they carry mutations aa substitution or deletions which do not alter the binding specificity of the antibody of the invention.

The invention obviously extends to the amino acid sequences of the Sequence Listing also when they comprise additional peptides positioned at the C or N-terminus, as for instance the "tag" or "flag" sequences which are useful for purification or immunological recognition of the recombinant antibody in its various forms or when they carry deletions at the C- or N-terminus, but which do not alter their binding specificity.

A particularly preferred type of "tag" sequence is the polyhistidine tail, coded by the expression vector used in the present invention, which is expressed at the C-terminal end of sequence ID NO:6 in order to facilitate affinity purification on a nickel column. Another sequence tag is the SV5 of SIV, which is added in order to facilitate immunological recognition.

A further aspect of the invention is represented by all the nucleotide sequences resulting from degeneracy of the genetic code, characterised by the fact that they code the scFv antibody with sequence ID NO:6, or the VH heavy chain corresponding to SEQ ID NO:4, or the light chain corresponding to SEQ ID NO:2, and the nucleotide sequences coding polypeptides having at least 95% homology preferably 98% or 99% homology with the SEQ ID NO:6, the SEQ ID NO:4, the SEQ ID NO:2, preferably with SEQ ID NO:4, or coding for their conservative variants. Therefore the nucleotide sequences identified with SEQ ID NO:1, 3, 5 of the Sequence Listing, or nucleotide sequences comprising such sequences, represent a particularly preferred embodiment of the nucleotide sequences of the invention.

Also included in the present invention are all the nucleotide sequences obtained by means of "parsimonious mutagenesis" (Shier, R., et al., 1996, Gene 169: 147) or by means of other methods of random or directed mutagenesis of nucleotide sequences of the present invention, in particular SEQ ID NO:1, 3, 5 (Marks, J. D., et al., 1992, J. Biol. Chem. 267: 16007) performed in order to improve some of properties of antibodies, as for instance the affinity, while maintaining binding specificity for the C5 cleavage site. Moreover the present invention includes all scFv antibodies in which the sequence coding the VII region, corresponding to SEQ ID NO:3, is maintained constant, while the sequence coding the VL region of antibody TS-A12/22, corresponding to SEQ ID NO:1, is replaced by "chain shuffling", for example using collections ("libraries") of VL human regions.

The nucleotide sequences object of the present invention are cloned in vectors suitable for their amplification, further mutagenesis or modification or expression. Therefore, the vectors containing at least one of the nucleotide sequences corresponding to SEQ ID NO:1, 3, 5, 7, 9, 11 as in the sequence listing represent a further aspect of the invention. These are preferably used for preparation of recombinant antibodies or of chimeric proteins in a suitable host and following methods known in the art.

In accordance to a preferred embodiment of the present invention, the recombinant antibodies are preferably cloned and expressed in prokaryotic hosts: particularly preferred is *E. coli*, but other prokaryotic hosts can also be used, such as *B. subtilis, P. pastoris, K. Lactis*, or eukaryotic cells of plant or animal origin. Expression vectors containing such nucleotide sequences are optimised for expression in each of these hosts, by insertion of suitable regulatory regions, promoters, transcriptional terminators or activators, or replication origin. A particularly preferred expression vector according to the present invention is represented by a periplasmic expression vector for *E. coli*, in particular the vector pDAN5 (Sblattero, D. and Bradbury A., 2000, Nat. Biotechnol. 18:75).

The antibody or the chimeric proteins having the specificity described in the present invention inhibit C5 conversion to its biologically active products. In particular, by blocking C5b formation they block formation of the terminal complex C (TCC) that leads to formation of the MAC (Membrane Attack Complex) which is capable of determining massive cellular lysis and significant tissue damage. Moreover, by inhibiting C5a formation they also inhibit the chemiotactic activity of C5a for Polymorphonuclear Leukocytes of and monocytes, that upon stimulation produce either cytokines such as IL-1, IL-6, IL-8, or other important inflammatory mediators such Serin-elastases, peroxidases, etc.

The C5a chemotactic activity and the cytolytic activity of MAC, to formation of which C5b participates, are considered the main causes of induced tissue damage in several inflammatory diseases. For instance, elevated levels of C5a fragment and of TCC have been found in the synovial fluid of patients with rheumatoid arthritis or in the cerebrospinal fluid of patients with several diseases of the central nervous system.

Therefore a further aspect of the invention relates to therapeutic use of recombinant anti-C5 antibodies of the invention, preferably human, carrying the ability of inhibiting the conversion of the C5 component to C5a and C5b, in one of the forms described in the invention: scFv, VH and/or VL alone or in combination with constant regions of Ig, preferably of human, rat or mouse origin, chimeric proteins or single variable regions and their conservative mutations, isotypic variants etc. This aspect also relates to therapeutic use of their preferred embodiments composed of the amino acid sequences SEQ ID NO:2, 4, 6 of the Sequence Listing.

In accordance to the invention, the antibodies block conversion of C5 by the C5 convertase. This enzyme can be activated by the classical pathway initiated by the C1q complement component triggered by antigen-antibody complexes or of IgG or IgM aggregates, or by the alternative activation pathway initiated by natural substances such as lectins, bacteria or yeast cell walls, or some snake venoms or nephritic factors. Therefore it has been assessed whether antibodies or proteins of the invention selectively block one or the other of the two complement activation pathways. Based on in vitro experiments performed by hemolytic assay on sheep erythrocytes (SRBC: Sheep Red Blood Cells) or on rabbit erythrocytes (RBC), the antibodies and proteins according to the present invention inhibit both classical and alternative complement activation pathways. An advantage provided by the use of antibodies or proteins having specificity for the C5 component in accordance to the present invention is that the initial complement components remain available for other functions of the complement system such as opsonization and clearance of immuno-complexes. This therapeutic approach turns out to be advantageous over a potential block at the level of the C3 component that precedes the action of the C5 component. A block at the level of the C3 component would lead to a total block of the complement cascade and of its functions in opsonization and clearance of immunocomplexes.

Therefore, in a particularly preferred embodiment, the antibodies or the proteins of the invention, in one of the described embodiments or in those obviously derivable from them, are used for pharmaceutical preparations for treatment of diseases caused or accompanied by hyper-activation of the complement system. The invention extends the use of antibodies and proteins of the invention, and their coding nucleotide sequences, to the diagnostic field, in the area of diagnosis of disorders characterised or accompanied by uncontrolled activation of the complement system, in particular of the C5 component or of its biologically active fragments.

More preferably, polypeptides and antibodies of the invention are used for treatment or prevention of diseases caused or accompanied by cytotoxic and pro-inflammatory action of the terminal C complex (Terminal C Complex TCC), wherein particular such diseases comprise chronic inflammation, and in particular rheumatoid arthritis, glomerulonephritis, multiple sclerosis, demyelinating peripheral neuropathies, atherosclerosis or some autoimmune disorders.

Moreover, experimental tests have demonstrated that anti-C5 polypeptides and antibodies of the invention are therapeutically useful in both treatment and prevention of acute inflammatory pathologies induced or accompanied by massive activation of the C5 component, which acts through the chemotactic activity of the C5a fragment, as well as through the TCC activity initiated by the C5b fragment. For instance, acute pathologies are represented by bacterial sepsis, tissue damage, for example damage of the myocardium, of the central nervous, damages due to transplantation or caused by ischaemia and re-perfusion after ischaemia.

Moreover, a further aspect of the invention concerns the therapeutic use of nucleotide sequences coding antibodies or proteins of the invention, or the vectors containing them. Those are preferably used in somatic gene therapy of diseases induced or accompanied by massive activation of the C5 component, by uncontrolled activation of the complement system, by excess production of C5a and C5b fragments, by excess production of complement components C5 to C9, as in rheumatoid arthritis or in some autoimmune disorders. Being subjected to individual variability and general health status, it is not easy to quantify a higher than normal level of activation of the complement system and of conversion of the activated C5 component to its biologically active fragments. Therefore abnormal levels are pragmatically defined as those that are able to cause an acute or chronic pathological state.

In vivo and in vitro production of antibodies of the invention in transgenic animals, obtained by genetic manipulation of non-human mammals using at least one of the nucleotide sequences described in the present invention by methods known to the expert of the field, is also comprised within the scope of the present invention. This represents a useful application to the study of genetic diseases characterised by insufficient production of C5a and C5b or by hyperactivation of complement components from C5 to C9.

Antibodies and proteins of the invention and their coding nucleotide sequences can be prepared for therapeutic use in the form of pharmaceutical compounds in combination with suitable excipients and/or diluents preferably for parenteral administration.

Moreover, the antibodies of the invention allow the preparation of diagnostic, therapeutic or research kits, where in such kits comprise at least one of the antibodies or of variable chains described in the invention, corresponding to sequences SEQ ID NO:2, 4, 6, or their homologous variants or fragments generated for diagnosis or prognosis of diseases characterised by hyperactivation of the C5 component or their encoding DNA sequences. The nucleotide sequences of the invention corresponding to sequences SEQ ID NO:1, 3, 5 and their homologous sequences, are preferably used to prepare kit for transfection of eukaryotic cells.

The present invention also comprises the realization of a kit for selecting compounds that interfere or modulate the cleavage of the alpha chain of the C5 complement component in its biologically active fragments. Realization of such kit involves the use of the polypeptides of the invention, preferably the VH chain (SEQ ID NO:4) or the scFv chain (SEQ ID NO:6) and at least one of the following polypeptides: C5 complement component and its alpha chain, or a peptide comprising the cleavage site for C5 convertase, preferably corresponding to sequence SEQ ID NO:15. The compounds can be identified, as an example, by means of a competitive assay detecting the inhibition of peptide-antibody binding using at least one of the sequences of the invention. The antibodies and polypeptides of the invention, independently from the fact that they originate from a human antibody library, are characterised by the ability to recognise the C5 complement component at the level of an epitope present in the alpha chain of the C5 component and comprising the cleavage region of C5 convertase. The binding specificity of the antibody of the invention for the epitope comprising the cleavage site for C5 convertase is situated between glycine 733 and arginine 734 in human C5, according to the SwissProt Data Base numbering (SEQ ID P01031). This epitope could be differently located in C5 of non-human mammalian species such as rat, mouse, rabbit; however it will be considered as having the same specificity, would it have the effect to block conversion of the respective C5 to C5a and C5b.

Therefore, according to a further aspect, the invention relates to the use of anti-C5 antibodies of the invention for setting up animal experimental models of diseases induced or accompanied by hyper-activation of the complement system and in particular of the C5 component.

In accordance with a further aspect, the invention comprises also the peptide of complement factor C5 pertaining to mammalian species, and preferably human, that comprises the cleavage site for C5 convertase. This peptide is preferably that comprising the region corresponding to amino acids 731-740 of the human mature protein. Even more preferably the peptide has sequence KDMQLGR↓LHMKTLLPVSK (SEQ ID NO:15), corresponding to amino acid sequence 727-744 of the human protein. The peptides according to this last aspect of the invention are used for preparation of medicaments, for example vaccines, or as immunogen to prepare antisera for prevention and treatment of pathological conditions involving uncontrolled activation of the C5 complement component, such as rheumatoid arthritis or some autoimmune disorders.

In accordance with this further aspect, the invention includes also the use of a peptide comprising the region corresponding to amino acid sequence 731-740 of the human mature protein, or of a peptide sharing at least 80% homology with such region, more preferably at least 90% or 95% or 98% homology including the corresponding regions of the C5 component of non-human mammals. Even more preferably, this aspect of the invention includes the use of a peptide having sequence KDMQLGR↓LHMKTLLPVSK (SEQ ID NO:15) (derived from the human protein) or of a peptide having at least 80%, more preferably at least 90% or 95% or 98% homology to such peptide, together with or in alternative to anti-C5 recombinant antibodies, in particular those comprising the variable region of the VH heavy chain, corresponding to SEQ ID NO:4, or the scFV antibody, corresponding to SEQ ID NO:6, to be used for selection of drugs and antibodies, even recombinant, capable of inhibiting conversion of activated C5 factor to its biologically active fragments C5a and C5b.

EXPERIMENTAL SECTION

Materials

Antibody library. The antibody library used, having a complexity of $7 \times 10^9$, was derived from human non-immune (naive) peripheral lymphocytes. The construction of this library is described in Sheets, M. D., et al., 1998, Proc. Natl. Acad. Sci. USA 95:6157.

Bacteria. Phage amplification was in *E. coli* strain DH5aF' (F'/endA1 hsdR17 (rK$^-$mK$^+$) supE44 thi-1 recA1 gyrA (Naf) relA1 D (lacZYA-argF) U169 deoR (F80dlacD(lacZ)M15)). For scFv fragment preparation was used *E. coli* strain HB2151 (K12, ara (lac-pro), thi/F' proA$^+$B$^+$, lackl$^q$ ZM15).

Purified proteins. Purified components C4 to C9 were purchased from Quidel (Saint Diego, Calif.) and the human recombinant C5a component was purchased from SIGMA-ALDRICH® S.r.l. (Milan, Italy). C5 alpha and beta subunits were Obtained by incubating 50 µg of C5 diluted in 0.55 M TRIS-HCl pH 8.1 containing DTT (0.02 M) for 30 min at room temperature (RT), followed by treatment with iodoacetamide (0.12 M) for 1 hour at RT. Alpha and beta chains were purified by gel filtration on Superose 12 (Pharmacia Biotech, Milan, Italy) in Fast Protein Liquid Chromatography (FPLC) and purity was assessed by SDS-PAGE in non-reducing conditions.

Sera. A serum lacking in the C5 complement component (C5D) was obtained from a patient with meningococcal infection. C5 levels were below detection and haemolytic activity was lacking in this serum, and was restored by addition of exogenous of C5. Human serum obtained from blood donors was used as a source of C5 factor.

Preparation of the intermediate EAC1-3b for hemolytic assay.

Sheep erythrocytes (SBRC: Sheep red blood cells) were sensitised with sub-agglutinating amounts of rabbit IgM (EA). The EAC1-3b intermediate for hemolytic reaction was prepared by incubating antibody-sensitised erythrocytes (EA) with 1/10 diluted C5 depleted serum (C5D) in salt buffer containing glucose and Veronal (GVBS). Incubation was performed for 70 minutes at 37° C., followed by addition of suramine (Bayer, FRG) to block the degradation reaction, as described by Harrison, R. A., and P. J. Lachmann (Harrison, R. A., and P. J. Lachmann. 1986. Complement technology. In Handbook of Experimental Immunology. D. M. Weir, L. A. Herzemberg, C. Blackwell, and A. Herzemberg Leonore, eds. Blackwell Scientific Publ, London.

Antisera. Two anti-C5a monoclonal antibodies (Oppermann et al. Complement Inflamm., 1991, 8:13) and a goat anti-C5 antiserum (Quidel, Saint Diego, Calif. U.S.A.).

Example 1

Amplification and Selection of Phage Library

Phages were obtained and amplified as described in Marks, J. D. et al., 1991, J. Mol. Biol. 222:581. The selection was performed in "immunotubes" (Nunc, Mascia Brunelli, MI, IT) coated with purified C5 protein. Coating of "immunotubes" was obtained by incubation with a C5 solution (10 µg/ml in PBS) overnight at 4° C. Phages were diluted in PBS containing 2% non-fat dry milk (MPBS) and incubated in immuno-tubes for 60 minutes at room temperature. After incubation, the immunotubes were washed 20 times with PBS containing 0.1% Tween 20 (PBST) and 20 times with PBS. The phage particles bound to immunotubes were eluted with 1 ml of *E. coli* bacterial culture at a density of 0.5 $OD_{600}$ for 30 minutes at 37° C. Ampicillin (75 µg/ml), helper phage and kanamycin (25 µg/ml) were then added and the culture was grown overnight.

After a second selection cycle on C5 coated immunotubes, eluted *E. coli* cells were amplified to extract phagemid DNA using methods known in the art. The extracted DNA was used as template for separate PCR amplifications of VH and VL regions, and subsequent assembly and cloning in pDAN5 vector (Sblattero, D., and Bradbury A., 2000, Nat. Biotechnol. 18:75). The pDAN5 vector is a phagemid vector containing lox and $His_6$ regions and the recognition region for the p27 SV5 protein of SIV virus, characterised by the fact that VH and VL regions inserted in the vector are expressed in VL-VH order, with the light chain at the N-terminus. After transformation with the phagemid, *E. coli* cells were incubated with the helper phage and phage particles were used for a third selection cycle. After elution, clones were analysed for their ability to bind C5 according to what is described in is Example 2.

Example 2

Isolation of Phage Particles with Binding Specificity for the C5 Antigen

The phage particles obtained after three cycles of C5 "panning" in immunotubes (as described in Example 1), were used to infect *E. coli* cells grown on solid medium. Single bacterial colonies were transferred in 96-well plates and the resulting phages were further tested by ELISA for their ability to bind C5. The C5 antigen, at a concentration of 10 µg/ml in 0.1 M bicarbonate buffer pH 9.6, was bound to the plates by overnight incubation at 4° C. After saturation of plates with MPBS (PBS containing 2% non-fat dry milk), 50 µl of phage suspension were diluted with an identical volume of MPBS; a monoclonal antibody anti-pIII (M13 protein) conjugated to HRP (Pharmacia Biotech) was then added. Positive binding was revealed by addition of $H_2O_2$ and 3,3',5,5'-thetramethyl-benzidine diclorate (SIGMA-ALDRICH®) as substrate and absorbance at 450 nm by spectrophotometric reading.

Positive clones by the ELISA assay were further selected on the basis of the difference of V region coding fragments. V regions were amplified using specific primers as described in Marks et al. (cited work), cleaved with BstNI and electrophoretically separated on 2% agarose gel. Twelve clones were isolated that proved to be different from each other based on their electrophoretic pattern.

Example 3

Preparation of Soluble Single Chain ScFv Antibodies

Phage clones obtained as described in Example 2 were used to infect the *E. coli* strain HB2151 to obtain expression of scFv fragments in soluble form. Bacteria grown until O.D. 0.5 in 2XYT medium, containing ampicillin, were induced with isopropil-β-tiogalattopiranoside and further grown for 5 hours. The periplasmic fraction containing scFv antibodies was prepared by incubation with B-PER reagent (Pierce, Celbio, MI, IT) for 20 minutes at RT, followed by centrifugation for 15 minutes at 27000×g. The supernatant was dialyzed against PBS and single chain antibodies containing the poly-histidine tail at the C-terminus were purified by affinity chromatography on nickel Ni-NTA resin (QIAGEN®, MI, IT).

The binding capacity of purified single-chain antibodies for factor C5 was verified by means of a solid-phase ELISA assay. This was analogous to that used for phage particles. Rather than the antibody directed at pIII of M13, the antibody used for detection was a monoclonal antibody against peptide SV5-tag expressed at the C-terminus of single chain antibodies.

The protocol for the ELISA assay was the following: wells of a 96 well microtiter plate were coated with antigen (purified C5, 250 ng) by overnight incubation at 4° C. in 0.1 M sodium bicarbonate buffer, pH 9.6 and then washed with PBS 0.1% Tween 20 (PBST). Residual binding sites were blocked with PBS containing 1% BSA for 1 hour at 37° C. Bacterial extracts or purified single chain scFv antibody (1 µg/ml) were then incubated and revealed with anti-SV5 tag antibody (diluted 1/1000) followed by goat anti-mouse IgG antibody (diluted 1/1000) during 1 hour incubation at 37° C. The enzymatic reaction was developed with p-nitrophenilphosphate (SIGMA-ALDRICH®; 1 mg/ml) as the substrate in 0.1M glycine buffer pH 10.4 containing, 1 mM $MgCl_2$ and 1 mM $ZnCl_2$, and adsorbace at 405 nm was read by the ELISA reader Titertek multiskan.

All purified scFv antibodies were found to be capable of binding factor C5 by the described ELISA assay.

Example 4

Determination of the Binding Affinity of scFv Ts-A12 Antibody for Factor C5 by Surface Plasmon Resonance (SPR)

The binding affinity of the Tsa-12 antibody, purified by means of FPLC on Superdex 75 (Pharmacia), for factor C5 was measured by means of BIACORE™ 2000 (a system that generates unique data on the interactions between proteins and other molecules). The microchip (CMS, Biacore) was prepared by direct conjugation of the C5 antigen with amines (20 µg/ml in 10 mM Sodium Acetate pH 4.5). The final level of immobilisation turned out to be approximately 1000 RU (Resonance Units). Association and dissociation of antibody molecules from the bio-chip were measured using an optical detection system (Surface Plasmon Resonance).

The analysis was carried out at 25° C., at a flow of 15 µl/min, using 4 different scFv concentrations in the range comprised between 100-300 nM, in PBS, 0.005% P20 (Biacore). The binding curves were interpolated 1:1 according to the model of Langmuir, using the dedicated software termed BIAevaluation (version 3.5) with correction for the mass transfer. Measurements performed on the equilibrium dissociation constant are reported in table 1.

TABLE 1

Rates of association and dissociation of scFV TS-A12 on purified C5 immobilized on chip.

| clone | $k_{on}$ ($10^5$ $s^{-1}$ $M^{-1}$) | $k_{off}$ ($10^{-3}$ $s^{-1}$) | $K_D$ ($10^{-9}$ M)$^a$ |
|---|---|---|---|
| TSA-12 | 1.3 | 0.026 | 200 |

$^a$The equilibrium constant was calculated as $K_D = k_{on}/k_{off}$

As it is shown in table 1, the KD calculated for the TS-A12 antibody turns out to be of $2 \times 10^{-7}$ M (sub-micromolar affinity), as expected for antibodies derived from collections (libraries) of non-immune antibodies.

Example 5

Increased Affinity of the TS-A12 Antibody by Means of "Chain Shuffling"

In order to increase the affinity, the TS-A12 antibody was subjected to substitution ("shuffling") of the VL light chains. For this purpose the phagemid DNA was cut with BssHII and SalI to excise the VL region. This region was substituted with all the repertoire of VL chains of a preimmune library (Sblattero, D., and Bradbury A., 2000, Nat. Biotechnol. 18:75) that was prepared with same enzymes. The library was subjected to three cycles of selection on the antigen, as described in examples 1 and 2, until a series of antibodies specific for C5 was obtained. Among those is TS-A12/22 having dissociation constant, as measured with BIACORE 2000 according to the method described in the previous example, of $1.8 \times 10^{-8}$ M, therefore with an increment of molar affinity of approximately one order of magnitude.

Example 6

Characterisation of the Inhibition from the Antibodies scFv AntiC5 of the Conversion of C5 to C5a The obtained anti-C5 scFv fragments were further characterised for their ability to inhibit the hemolytic activity of C5 or, in other words, to block conversion of the C5 component to C5a. For this purpose, a small amount of purified C5 component was incubated, for 30 minutes at RT, with purified scFv anti-C5 antibodies, or with an unrelated scFv (anti-gliadin), or with VBS (Veronal Buffer Saline) as control. The mixture was then added to sheep erythrocytes sensitised with sub-agglutinating amounts of rabbit IgM (EA) (see Harrison, R, A., and P. J. Lachmann. 1986. Complement technology. In Handbook of Experimental Immunology. D. M. Weir, L. A. Herzemberg, C. Blackwell, and A. Herzemberg Leon ore, eds. Blackwell Scientific Publ, London) coated with components from C1 until C3b (EAC1-3b) that allow to reveal C5 activation through the classical pathway. The erythrocyte suspension was re-suspended in C5 depleted serum (C5D) and incubated for 30 minutes at 37° C. At the end of this procedure, cell lysis was measured as percentage of the control of total lysis in distilled $H_2O$ (see FIG. 1, panel B). The inhibition of C5a and TCC production by the scFv TS-A12 and TS-A12/22 was measured by means of ELISA using the monoclonal antibody 17/5 as the capture antibody and antibody G25/2 as detection antibody according to what has been described in Opperman et al., 1991, Complement Inflamm. 8:13. The presence of TCC was measured using antibody aE11 as the capture antibody and a biotinylated anti-C5 antibody (SIGMA-ALDRICH®) followed by alkaline phosphatase-conjugated streptavidin, as described by Tedesco et al. (1997, J. Exp. Med. 185:1619).

Figure 1:
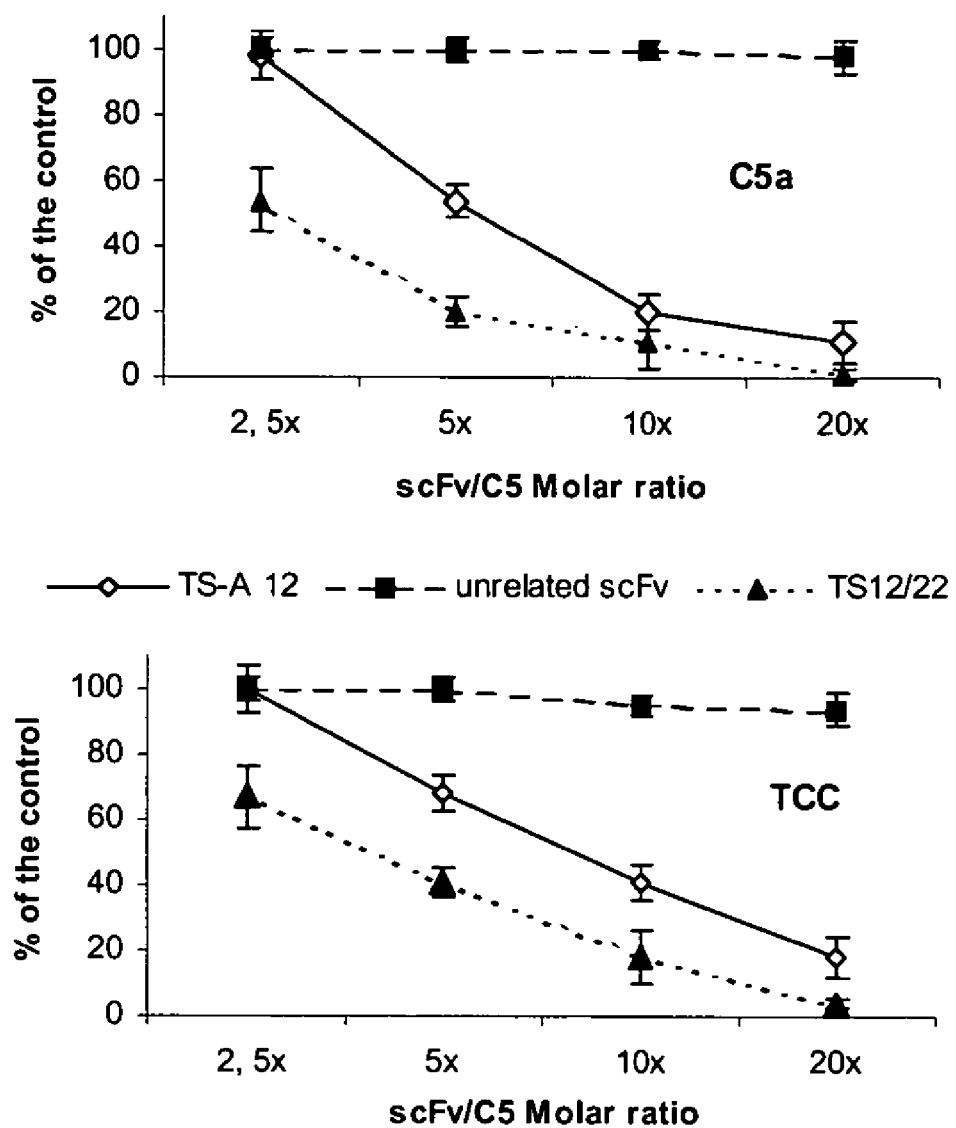
FIG. 1. Assessment of the ability of anti-C5 clones scFv Ts-a12 and Ts-a12/22 to inhibit formation of C5a fragment by means of an ELISA assay (panel A) and an haemolytic assay (panel B).

The results of the test are presented in FIG. 1, where it is shown that antibodies TS-A12 and TS-A12/22 inhibit almost completely formation of C5a (FIG. 1A) (classical pathway) and of TCC (FIG. 1B) whereas the other isolated scFv are effective only partially or to a limited extent. The presence of VBS or of an unrelated scFv in the reaction mixture did not show, as expected, any inhibitory effect.

Example 7

Determination of the Sequence of TS-A12/22 Antibody

The VH and VL fragment of positive clones was compared with known antibody sequences published in the VBASE data bank. The VH heavy chain of TS-A12/22 antibody was found to be derived from the VH3/V-48 chain and the light chain from Vλ3/V-2-14. The DNA sequence coding the scFV TS-A12/22 antibody is reported in the Sequence Listing as SEQ ID NO:5, and the derived amino acid sequence as SEQ ID NO:6.

Example 8

Mapping of the Recognition Site of the TS-A12122 Antibody on the C5 Molecule It was first characterised, by means of the Western-blotting technique, whether the TS-A12/22 antibody recognises the alpha or beta of subunit of the C5 complement component prepared as described in Materials. Briefly the two subunits were electrophoresed in separate wells and transferred on nitrocellulose membranes. A solution containing Tris 50 mM pH 7.6, 0.5 M NaCl and 4% skimmed powder milk was used to block non-specific sites for 1 hour at 37° C. Membranes were revealed by incubation with a suitable dilution of the TS-A12/22 antibody for 1 hour at 37° C., followed by incubation with a secondary antibody labeled with alkaline phosphatase or with streptavidin conjugated with alkaline phosphatase (SIGMA-ALDRICH®). The enzymatic reaction was developed with blue tetrazolium and 5-bromo-4-chlorine-3-indolil phosphate (SIGMA-ALDRICH®, 0.30 mg/ml) diluted in 0.1 M Tris-HCl pH 9.5 containing 0.1 M NaCl and 5 mM $MgCl_2$. Rainbow RPN 756 (AMERSHAM™ Italy (a trademark of General Electric Healthcare Limited)) were used as molecular weight markers. As it is shown in FIG. 2, the TS-A12/22 antibody of the invention recognises the alpha sub-unit of the C5 factor, loaded in lane 1, while does not recognise the beta sub-unit, loaded in lane 2.

Since the purified TS-A12/22 antibody also inhibited hemolytic activity due to inhibition of the conversion of C5 to C5a, as demonstrated in example 9, the hypothesis that the antibody might recognise as binding site the cleavage site for C5 convertase was then verified.

In order to verify this hypothesis, a peptide of 18 amino acids was synthesised, with sequence: KDMQLGR↓LHMKTLLPVSK (P5A-18 also termed C5cs comprising SEQ ID NO:15). This peptide corresponds to region 727-744 of the mature protein and comprises the cleavage site of C5 convertase (indicated by the arrow) between glycine 733 and arginine 734 according to SwissProt numbering for human C5 (SEQ ID P01031). The peptide was used in a competitive ELISA assay on the C5 protein on solid phase. Before binding to the solid phase, the TS-A12/22 antibody was pre-incubated with the P5A-18 peptide, corresponding to amino acids 727-744 of the C5 component, or with an unrelated peptide of sequence GEEIQIGHIPRED-VDYHLYP (SEQ ID NO:16 of sequence listing) corresponding to a fibronectin derived peptide termed CS5.

In FIG. 3 are shown the results that were obtained: the P5A-18 peptide inhibited binding of the TS-A12/22 antibody to C5, and this inhibition was dose-dependent, ranging from 45% to 90% for peptide concentrations of 200 ng and 800 ng/200 respectively. This result confirms that the TS-A12/22 antibody recognises just this region on the activated factor C5. The concentration values correspond to a peptide Ki of 1 μM, that is not different from the $K_D$ measured by SPR for the entire protein, according to what has been described in example 4.

As expected, both the unrelated peptide CS5 and the whole C5 protein resulted to be ineffective in inhibiting the binding of TS-A12/22 antibody to activated C5, even at the highest concentrations used, thus indicating that inhibition by peptide C5cs (P5a-18) was specific for the alpha chain of C5.

Example 9

Functional Characterisation of Antibody TS-A12/22. Inhibition of Hemolytic Activity and TCC Activation Having assessed the characteristics of the inhibition of the classical activation pathway of factor C5 by the TS-A12/22 antibody, it was then verified whether there was inhibition also of the alternative pathway of C5 activation, and at which level. The test was carried out using rabbit erythrocytes as the target cells, according to well-known methods. Briefly, increasing amounts of C5 were mixed with 600 ng of the scFv of the invention or with an unrelated scFv or with GVBS in which scFv antibodies have been solubilised, and then incubated for 15 minutes at room temperature. In order to estimate the classical pathway of complement activation, each mixture was added to a 1% suspension of sheep erythrocytes sensitised with rabbit antibody and coated with complement component up to C3b, termed EAC1-3b. In order to estimate the alternative pathway of complement activation, each mixture was added to a 1% suspension of rabbit erythrocytes.

C5 depleted serum diluted 1/200 was added to each erythrocyte suspension. After incubation for 30 minutes at 37° C., the percentage of erythrocyte lysis was measured by comparison to a 100% value obtained by lysing erythrocytes with an equal volume of distilled of $H_2O$ and to a blank consisting of erythrocytes re-suspended in GBVS. Spectrophotometric reading was performed at 412 nm and the results are reported in FIG. 4: inhibition of EAC1-3b lysis through the classical pathway (A Panel); inhibition of lysis of rabbit erythrocytes through the alternative pathway (B Panel). The TS-A12/22 antibody inhibits rabbit erythrocyte lysis by inhibiting C5 conversion similarly through the classical pathway and the alternative pathway.

Since the amino acid sequence corresponding to the cleavage site of convertase on the C5 alpha chain is conserved in several animal species, it was furthermore evaluated, by hemolytic assay, the ability of TS-A12/22 antibody to inhibit conversion of C5 to C5a also in rabbit, mouse and rat sera. The TS-A12/22 antibody was capable of inhibiting the hemolytic activity present in the serum of all animal species tested, though with different efficiency. These results are reported in FIG. 5, showing that the efficiency of inhibition of rat serum was practically similar to that of human serum, whereas the efficiency was higher on rat or rabbit serum. It should be also considered that a higher amount of rabbit serum was necessary to induce a percentage of lysis comparable to that induced by human C5.

(The specificity of TS-A12/22 antibody was evaluated also on other components of the complement cascade, as for instance C3 and C4, which are structurally similar to C5, but cross-reactivity was not found).

Example 10

In Vivo Use of TS-A12/22 Antibody

In order to test the effect of the TS-A12/22 antibody in vivo, the influx of PMN was measured in the rat joint injected with BSA, BSA and TS-A12/22 or BSA and unrelated antibody. It was thus demonstrated that PMN chemotaxis, that is their number in the joint wash out liquid, was significantly reduced in presence of TS-A12/22 compared with rats treated with BSA or with BSA and unrelated antibody (FIG. 6). Moreover the deposition of the C3 and C9 complement components was checked on a histological section of the joint of the back paw of treated rats, by immunofluorescence with specific antisera and fluorescein-conjugated secondary antibody (FIG. 7). It was found that C3 deposition remained unchanged as result of the administration of BSA plus TS-A12/22 antibody or of unrelated antibody, but the deposition of C9 was strongly inhibited in presence of TS-A12/22. It was thus confirmed that the TS-A12/22 antibody inhibits the complement cascade at a step intermediate between C3 and C9 and therefore at the level of the conversion of C5 to C5a+C5b.

Example 11

Dimerization of scFvTS-A12/22 Antibody

The sequence of the TS-A12/22 antibody was modified by the addition of CH3 or CH2-CH3 domains to the C-terminal end and of an eukaryotic leader sequence to the N-terminal end.

These modifications were aimed at:

inducing scFv dimerization, by forming a structural complex, in order to increase the valence from one to two and to increase the stability of the antibody (hereafter defined "minibody"). Based on the different types of cloning, covalent bonds are not formed between subunits of the dimer in constructs comprising only CH3, while in those comprising CH2-CH3 domains are formed two disulfide bridges between cysteines of the CH2 hinge region of the two monomers;

making possible the production of minibodies in mammalian cell cultures with increments of the yield and absence of bacterial contaminants at the end of extraction and purification procedures;

creating the conditions for an in vivo analysis of the biological activity of the minibody in animal models, minimising the host immune response by adding CH3 and CH2-CH3 domains from the same species as the treated animal (mouse or rat).

The above described modifications have been performed in two steps. First the scFv was cloned into plasmid vector pUT (Li E, et al. 1997. Protein Eng. 10:731-6) conveniently modified in order to allow insertion of the leader sequence and of a human CH3 domain. The CH3 human domain was then replaced with a series of constructs of domains from other species, as reported below. Finally, a fragment of pUT vector comprising the minibody in various versions, was cloned in the commercial vector pcDNA3 (Invitrogen), and was tested for expression in cultured cell.

For this, the pUT vector containing an unrelated scFv was modified by replacing the recognition site for the restriction enzyme (RE) BspEI, located at the end of the VH chain, with the BssH2 site. The BspEI substitution was performed by inverse PCR done with the primers reported in Table 2 (references A and B).

The mouse CH3 sequence present in pUT vector was then replaced with an analogous human sequence amplified by use of reference primers 1 and 2. Primer 2 inserts in addition a SV5 tag sequence (recognised by mAB SV5), and the cloning sites SpeI, PvuI and EcoRI. cDNA from human B lymphocytes was used as template and insertion into pUT was performed by restriction with the RE BssHII and PvuI and subsequent ligation of vector and fragment.

As indicated in FIG. 8, Fc domains of human, mouse and rat antibodies were inserted into the pUT vector that had been modified as described in the previous point. The original sequences of CH2 and CH3 domains were obtained from an NIH nucleotide database using accession numbers:

*Homo sapiens* J00220 (locus: IgA1 heavy chain gene)
*Homo sapiens* AF237583 (locus: IgG1 heavy chain gene)
*Mus musculus*: L27437 (locus: Immunoglobulin gamma heavy chain)
*Rattus norvegicus* M28671: (locus: RATIGG2B).

Primers reported in Tab. 2 and cDNA from B lymphocytes of the corresponding species were used for PCR cloning. The cloning in pUT was performed by BssHII and SpeI restriction and ligation after removal of the previous sequence (human CH3).

The scFv sequence was cloned into a series of pUT vectors containing Fc domains of different species described in the previous point, by means of PCR with a mix of universal oligonucleotides for amplification of known human scFv (see Sblattero D. and Bradbury A, Immunotechnology, 1998, 3:271-278, and reported in table 3), followed by digestion with ApaLI and BssHII restriction enzymes (RE).

Cloning in pcDNA vector of the constructs obtained in pUT was done by digestion with HindIII and EcoRI enzymes, selective recovery of the corresponding fragment and cloning in pcDNA3 that was cut with the same RE (see outline in FIG. 8).

TABLE 2

| Primers used for amplification of the Indicated Fc regions (Ra = rat; Mo = mouse; Hu: human). | | | |
|---|---|---|---|
| Name | Orient. | Sequence | |
| A<br>SEQ. ID No. 17 | PUT-ApaII | sense | 5'ATC CGA GTGCAC ACC TGT GGA GAG AAA GGC AAA G 3' |
| B<br>SEQ ID No. 18 | PUT-BsshII | antisense | 5'TCC TCA GCGCGC GGC TCT GGT GGC AGA CCG AAG G 3' |
| 1<br>SEQ. ID No. 19 | HuGCH3-s | sense | 5'CAG GCG GCG CGC GGG CAG CCC CAG GAA CCA CAG 3' |
| 2<br>SEQ. ID No. 20 | HuGCH3-a | antisense | 5' A CGT CGA TCG CCT GCT GAA TTC TTA AGT ACT ATC CAG GCC CAG CAG TGG GTT TGG GAT TGG TTT GCC ACT AGT TTT ACC CGG GGA CAG GGA GAG |
| 3<br>SEQ. ID No. 21 | HuGCH2-s | sense | 5' AG GCG GCG CGC GAC AAA ACT CAC ACA TGC CCA CCG TGC CCA 3' |
| 4<br>SEQ. ID No. 22 | HuA-CH2-s | sense | 5'CAG GCG GCG CGC GTT CCC TCA ACT CCA CCT ACC |
| 5<br>SEQ. ID No. 23 | HuA-CH3a | antisense | 5'CC GCT ACT AGT TTT ACC CGC CAA GCG GTC GAT |
| 6<br>SEQ. ID No. 24 | MoG-CH3-s | sense | 5'CAG GCG GCG CGC GGC AGA CCG AAG GCT CCA C |

TABLE 2-continued

Primers used for amplification of the Indicated Fc regions (Ra = rat; Mo = mouse; Hu: human).

| | Name | Orient. | Sequence |
|---|---|---|---|
| 7<br>SEQ. ID No. 25 | MoG-CH3-a | antisense | 5'CC GCT ACT AGT TTT ACC AGG AGA GTG GGA GAG |
| 8<br>SEQ. ID No. 26 | MoGCH2-s | sense | 5'CAG GCG GCG CCG GGT TGT AAG CCT TGC ATA TGT ACA |
| 9<br>SEQ. ID No. 27 | RaGCH3-s | sense | 5'CAG GCG GCG CGC GGG CTA GTC AGA AAA CCA CAG |
| 10<br>SEQ. ID No. 28 | RaGCH3-a | antisense | 5'CC GCT ACT AGT TTT ACC CGG AGG CCG GGA GAT G |
| 11<br>SEQ. ID No. 29 | RaGCH2-s | sense | 5' CAG GCG GCG CCG CAC AAA TGC CCT ACA TGC CCT |

TABLE 3

Universal Oligonucleotides mix for amplification of scFv of human origin

| Name | Orientation | Sequence |
|---|---|---|
| VL1<br>SEQ. ID No. 30 | sense | caggt gtgcac tcg gac atc crg dtg acc cag tct |
| VL2<br>SEQ. ID No. 31 | sense | caggt gtgcac tcg gat att gtg wtg acn cag wct |
| VL3<br>SEQ. ID No. 32 | sense | caggt gtgcac tcg cag cct gtg ctg car yc |
| VL4<br>SEQ. ID No. 33 | sense | caggt gtgcac tcg tcc tat gwg ctg acw cag cca |
| JH1<br>SEQ. ID No. 34 | antisense | gaccc gcgcgc gga gac rgt gac cag ggt |
| JH2<br>SEQ. ID No. 35 | antisense | gaccc gcgcgc aga gac ggt gac crt kgt |

Example 12

Production and Validation of the TSA12/22-CH2-CH3 Rat Minibody pcDNA plasmid carrying the construct for the TSA12/22 antibody, in the version containing CH2-CH3 domains, was used for in vitro transfection of the HEK 293 cell line. After treatment with DNA and lipofectin, cells were selected in presence of the antibiotic G418. After two weeks in culture, single cell clones were assayed for antibody production by detection of the activity in the supernatant. One clone was chosen and expanded for massive production of the TSA12/22-CH2-CH3 minibody. Purification of the minibody was carried out by chromatography.

Purified TSA12/22 antibody in the version containing the rat CH2-CH3 domains (minibody TSA12/22 CH2CH3) was tested for its ability to inhibit the classical complement activation pathway in an in vitro test, according to the modalities already described in the previous examples. In the diagram of FIG. 9 it is reported the percentage of inhibition of lysis of rabbit erythrocytes sensitized with IgM, mediated by complement in presence of fixed concentrations of scFv TSA12/22, of an unrelated scFv, of GVBS buffered salt solution and of the minibody composed of scFv TSA22/12 and rat CH2-CH3 domains.

The Tsa12/22-CH2-CH3 construct showed significantly better inhibitory activity than the corresponding scFv, as can be noticed in FIG. 9.

In vivo activity tests in the rat joint space were also performed. Arthritis was induced at time t=0 by intra-articular injection of methyl-BSA (bovine serum albumin) after the animal had been previously immunized with methyl-BSA. Therapeutic treatments with the minibody were performed by intra-articular injection at t=0 and 6 days after induction of arthritis. Efficiency of treatment was measured as number of polymorphonuclear leukocytes present in the intra-articular wash out and as reduction of joint swelling, as can be noticed in FIG. 10 where it is reported the course of PMN (polymorphonuclear leukocytes) recruited to the rat joint space in response to BSA-induced inflammation. The lower percentage of cells in presence of TSA22/12 CH2CH3 minibody, at two time points considered, indicates a reduction of the inflammatory process. FIG. 11 reports the inhibitory effect of the TSA22/12 CH2CH3 minibody on the extent of joint swelling caused by the inflammatory reaction. The measurements performed after 20 days assessed a therapeutic effect of the minibody also in the long term, either when it was administered together with BSA or 6 days later.

CONCLUSIONS

ScFv antibodies, isolated as described in example 1, were found to be able to bind to factor C5, as assessed by ELISA assay and as expected from the type of selection or "panning" of phage particles performed on C5. However not all ScFv antibodies were able to inhibit conversion of C5 to C5a+C5b, and therefore the biological functions following their activation. Because it binds in proximity of the C5 convertase cleavage site on the alpha chain of the activated C5 component and prevents production of C5a and C5b, the TSA12/22 antibody inhibits the chemotactic activity induced by the former and the hemolytic activity mediated by C5b through MAC formation. This inhibition operates downstream of the activation of the C3 component, therefore it is independent from the type of complement activation pathway utilised (classical or alternative).

Moreover, the TSA12-22 antibody dimerized by means of rat CH2 and CH3 domains (minibody) turned out to be particularly active in the long term treatment.

The invention claimed is:

1. A human antibody having specificity for a C5 alpha chain of a C5 component of the complement system characterized in that it recognizes a region corresponding to sequence 727-744 (SEQ ID NO: 15) of the C5 component of human complement or a region having at least 80% homology thereto, wherein said antibody inhibits the conversion of the C5 alpha chain to C5a and C5b, wherein a light chain of the antibody is a lambda chain or a kappa chain, and a variable region of a heavy chain is the VH3 region.

2. The antibody according to claim 1 characterized in that it is recombinantly produced.

3. The antibody according to claim 2, characterized in that it is in the form of single chain (scFv) comprising one variable region of the light chain covalently joined to one variable region of the heavy chain.

4. The antibody according to claim 1, characterized in that it comprises at least one of the amino acid sequences selected from the group consisting of: SEQ ID NO:2, 4, and 6.

5. The antibody according to claim 4 having amino acid sequence SEQ ID NO: 6.

6. The antibody according to claim 4 characterized in that it comprises both the amino acid sequences identified as SEQ ID NO: 2 and SEQ ID NO: 4, or their conservative mutations.

7. The antibody according to claim 4 characterized in that it comprises at least one of the sequences selected from the group consisting of SEQ ID NO: 2, 4, and 6 in combination with a sequence derived from an immunoglobulin heavy chain constant region.

8. The antibody according to claim 7 characterized in that it is dimeric.

9. A chimeric antibody characterized in that it comprises at least one of the sequences corresponding to SEQ ID NO: 2, 4, 6, 8, or 12, wherein the antibody recognizes a region corresponding to sequence 727-744 (SEQ ID NO:15) of the C5 component of human complement or a region having at least 80% homology thereto.

10. A pharmaceutical composition comprising as the active principle the human antibody of claim 1.

11. The composition according to claim 10 for myocardium reperfusion.

12. A composition comprising any one of the antibodies selected from the group consisting of: an antibody against the activated C5 component of the complement system which recognizes a polypeptide having at least 80% homology with the peptide comprising the region corresponding to sequence 727-744 of the C5 component of human complement, said peptide having the sequence KDMQLGR↓LHMKTLLPVSK (SEQ ID NO: 15) and wherein said antibody inhibits the conversion of the C5 alpha chain to C5a and C5b; an antibody comprising an amino acid sequences selected from the group consisting of: SEQ ID NO: 2, 4, and 6, or each one of SEQ ID NO: 7, 8, and 9.

13. The antibody according to claim 1, characterized by the lambda chain being Vλ3/V2-14.

14. The antibody according to claim 1, characterized by the kappa chain being Vκ4/DPK24.

15. The antibody according to claim 1, characterized by the VH3 region being VH3/V-48.

16. The human antibody of claim 1 or the chimeric antibody of claim 9 further comprising a peptide tag positioned at the C or N-terminus of said antibody or chimeric antibody, wherein said tag does not alter binding specificities of said antibody or chimeric antibody.

17. The antibody or the chimeric antibody of claim 16, wherein said tag facilitates affinity purification.

18. The human antibody or the chimeric antibody of claim 17, wherein said tag is a poly-histidine tag.

* * * * *